(12) United States Patent
Yamazaki

(10) Patent No.: US 11,490,798 B2
(45) Date of Patent: Nov. 8, 2022

(54) ENDOSCOPE SYSTEM, ENDOSCOPE APPARATUS, LIGHT SOURCE APPARATUS, AND METHOD OF OPERATING ENDOSCOPE SYSTEM

(71) Applicant: OLYMPUS CORPORATION, Tokyo (JP)

(72) Inventor: Kenji Yamazaki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 129 days.

(21) Appl. No.: 16/666,730

(22) Filed: Oct. 29, 2019

(65) Prior Publication Data
US 2020/0060531 A1    Feb. 27, 2020

Related U.S. Application Data

(63) Continuation of application No. PCT/JP2018/007566, filed on Feb. 28, 2018.

(30) Foreign Application Priority Data

May 2, 2017  (JP) .............................. JP2017-091624

(51) Int. Cl.
*A61B 1/06* (2006.01)
*A61B 1/00* (2006.01)
*A61B 1/045* (2006.01)

(52) U.S. Cl.
CPC .......... *A61B 1/0653* (2013.01); *A61B 1/0005* (2013.01); *A61B 1/00009* (2013.01);
(Continued)

(58) Field of Classification Search
CPC . A61B 1/0653; A61B 1/00009; A61B 1/0005; A61B 1/045; A61B 1/0638
See application file for complete search history.

(56) References Cited

U.S. PATENT DOCUMENTS 9,565,399 B2 *  2/2017  Kubo .......................... G06T 5/50
10,031,070 B2 *  7/2018  Chiba .................. A61B 5/1459
(Continued)

FOREIGN PATENT DOCUMENTS

JP           3228627 B2    11/2001
JP        2002-095635 A     4/2002
(Continued)

OTHER PUBLICATIONS

International Search Report dated Apr. 24, 2018 issued in PCT/JP2018/007566.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope system includes a light source configured to generate violet light, blue light, green light, and red light, a filter switching mechanism configured to change a spectrum of the green light emitted from the light source, a light amount adjustment circuit configured to respectively adjust light amounts of lights in three colors, that is, the violet light, the blue light, and the red light, an image sensor configured to pick up an image of an object illuminated with the green light including the spectrum changed by the filter switching mechanism and the lights in the three colors respectively including the light amounts adjusted by the light amount adjustment circuit, and a highlighting processing circuit configured to subject an image obtained by image pickup of the object illuminated with the green light including the spectrum changed by the filter switching mechanism to highlighting processing.

9 Claims, 10 Drawing Sheets

(52) U.S. Cl.
CPC ............ *A61B 1/045* (2013.01); *A61B 1/0638* (2013.01); *A61B 1/0646* (2013.01)

(56) References Cited

U.S. PATENT DOCUMENTS

| | | | |
|---|---|---|---|
| 10,426,325 B2* | 10/2019 | Chiba | A61B 1/0638 |
| 10,631,720 B2* | 4/2020 | Igarashi | A61B 1/00045 |
| 10,799,102 B2* | 10/2020 | Kamee | A61B 1/0661 |
| 10,939,799 B2* | 3/2021 | Kamon | A61B 1/3137 |
| 10,959,606 B2* | 3/2021 | Endo | A61B 1/00059 |
| 2003/0139650 A1* | 7/2003 | Homma | A61B 1/0638 |
| | | | 600/181 |
| 2003/0176768 A1* | 9/2003 | Gono | A61B 5/0084 |
| | | | 600/109 |
| 2003/0229270 A1* | 12/2003 | Suzuki | G02B 23/2469 |
| | | | 600/178 |
| 2007/0153542 A1* | 7/2007 | Gono | A61B 1/00009 |
| | | | 362/574 |
| 2009/0141125 A1* | 6/2009 | Yamazaki | A61B 1/00186 |
| | | | 348/70 |
| 2010/0067002 A1* | 3/2010 | Ishii | A61B 1/0638 |
| | | | 356/317 |
| 2011/0230715 A1* | 9/2011 | Saito | G06T 7/0012 |
| | | | 600/109 |
| 2011/0237915 A1* | 9/2011 | Yamaguchi | A61B 5/14551 |
| | | | 600/339 |
| 2012/0053434 A1* | 3/2012 | Saito | A61B 1/063 |
| | | | 600/324 |
| 2012/0197077 A1* | 8/2012 | Kaku | A61B 1/0669 |
| | | | 600/109 |
| 2012/0253157 A1* | 10/2012 | Yamaguchi | A61B 5/1459 |
| | | | 600/328 |
| 2013/0018242 A1* | 1/2013 | Yamaguchi | A61B 5/14551 |
| | | | 600/339 |
| 2015/0099932 A1* | 4/2015 | Morimoto | A61B 1/00057 |
| | | | 600/180 |
| 2017/0293134 A1* | 10/2017 | Otterstrom | A61B 1/00105 |
| 2018/0000334 A1* | 1/2018 | Morishita | A61B 1/04 |
| 2019/0215925 A1* | 7/2019 | Tanaka | G06T 11/001 |

FOREIGN PATENT DOCUMENTS

| | | |
|---|---|---|
| JP | 2013-017769 A | 1/2013 |
| JP | 2015-070946 A | 4/2015 |
| JP | 2015-231467 A | 12/2015 |
| WO | WO 2016/151672 A1 | 9/2016 |

* cited by examiner

ENDOSCOPE SYSTEM, ENDOSCOPE APPARATUS, LIGHT SOURCE APPARATUS, AND METHOD OF OPERATING ENDOSCOPE SYSTEM

CROSS REFERENCE TO RELATED APPLICATION

This application is a continuation application of PCT/JP2018/007566 filed on Feb. 28, 2018 and claims benefit of Japanese Application No. 2017-091624 filed in Japan on May 2, 2017, the entire contents of which are incorporated herein by this reference.

BACKGROUND OF THE INVENTION

1. Field of the Invention

The present invention relates to an endoscope system, an endoscope apparatus, a light source apparatus, and a method of operating the endoscope system, and particularly to an endoscope system used when observation in a living body is performed, an endoscope apparatus, a light source apparatus, and a method of operating the endoscope system.

2. Description of the Related Art

In endoscope observation in a medical field, a technique applicable to diagnosis of a lesion existing in an intermediate mucosal layer of a living tissue and a deep portion of a mucous membrane corresponding to a deep mucosal layer as a deeper layer than the intermediate mucosal layer has been conventionally proposed.

More specifically, Japanese Patent Application Laid-Open Publication No. 2002-95635 discloses a method of irradiating a living tissue with green narrow band light to obtain a band image having tissue information in an intermediate layer of the living tissue. For example, Japanese Patent Application Laid-Open Publication No. 2002-95635 discloses a method of irradiating the living tissue with red narrow band light to obtain a band image having tissue information in a deep layer of the living tissue.

For example, a method of subjecting an image obtained by image pickup of a living tissue to predetermined image processing to highlight a slight change of a color tone that occurs due to existence of a lesion in a deep portion of a mucous membrane of the living tissue.

SUMMARY OF THE INVENTION

An endoscope system according to an aspect of the present invention includes a light source configured to generate violet light, blue light, green light, and red light, a filter switching mechanism configured to change a spectrum of the green light emitted from the light source to any one of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane, in a wavelength band having a high absorbance by hemoglobin, a light amount adjustment circuit configured to respectively adjust light amounts of lights in three colors, that is, the violet light, the blue light, and the red light with a light amount of the green light including the spectrum changed by the filter switching mechanism as a reference, an image sensor configured to pick up an image of return light from an object illuminated with the green light including the spectrum changed by the filter switching mechanism and the lights in the three colors respectively including the light amounts adjusted by the light amount adjustment circuit, and a highlighting processing circuit configured to subject an image acquired by the image sensor to predetermined highlighting processing.

An endoscope apparatus according to an aspect of the present invention includes a light source configured to generate violet light, blue light, green light, and red light, a filter switching mechanism configured to change a spectrum of the green light emitted from the light source to any one of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin, a light amount adjustment circuit configured to respectively adjust light amounts of lights in three colors, that is, the violet light, the blue light, and the red light with a light amount of the green light including the spectrum changed by the filter switching mechanism as a reference, and a highlighting processing circuit configured to subject an image acquired with an image sensor by image pickup of return light from an object illuminated with the green light including the spectrum changed by the filter switching mechanism and the lights in the three colors respectively including the light amounts adjusted by the light amount adjustment circuit to predetermined highlighting processing.

A light source apparatus according to an aspect of the present invention includes a light source configured to generate violet light, blue light, green light, and red light, and a filter switching mechanism configured to change a spectrum of the green light emitted from the light source to any one of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin.

A light source apparatus according to an aspect of the present invention is a light source apparatus that generates, to observe an object by an image generated by a processor configured to subject an image generated by an image sensor configured to pick up an image of return light from the object illuminated with illumination light to highlighting processing, the illumination light to the object, the light source apparatus including a light source configured to generate violet light, blue light, green light, and red light, and a filter switching mechanism configured to change a spectrum of the green light emitted from the light source to any one of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin, while respectively adjusting light amounts of lights in three colors, that is, the violet light, the blue light, and the red light with a light amount of the green light including the changed spectrum as a reference.

An endoscope system according to an aspect of the present invention includes a light source configured to generate green light and light in a predetermined color different from the green light, a filter switching mechanism configured to change a spectrum of the green light emitted from the light source to any one of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin, a light amount adjustment circuit configured to adjust a light amount of the light in the predetermined color with a light amount of the green light including the spectrum changed by the filter switching mechanism as a reference, an image sensor configured to pick up an image of return light from an object illuminated with the green light including the spectrum changed by the filter switching mechanism and the light in the predetermined color including the light amount adjusted by the light amount adjustment circuit, and a highlighting processing circuit configured to subject an image acquired by the image sensor to predetermined highlighting processing.

An endoscope system according to an aspect of the present invention includes a first light source as a light source configured to generate green light and configured to generate the green light including any one of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin, a second light source configured to generate light in a predetermined color different from the green light, a light amount adjustment circuit configured to adjust a light amount of the light in the predetermined color with a light amount of the green light generated by the first light source as a reference, an image sensor configured to pick up an image of return light from an object illuminated with the green light generated by the first light source and the light in the predetermined color including the light amount adjusted by the light amount adjustment circuit, and a highlighting processing circuit configured to subject an image acquired by the image sensor to predetermined highlighting processing.

A method of operating an endoscope system according to an aspect of the present invention includes generating violet light, blue light, green light, and red light from a light source, changing a spectrum of the green light emitted from the light source to any one of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin, respectively adjusting light amounts of lights in three colors, that is, the violet light, the blue light, and the red light with a light amount of the green light including the changed spectrum as a reference, picking up an image of return light from an object illuminated with the green light including the changed spectrum and the lights in the three colors respectively including the adjusted light amounts, and subjecting an image obtained by image pickup of the return light to predetermined highlighting processing.

DETAILED DESCRIPTION OF THE PREFERRED EMBODIMENTS

Embodiments of the present invention will be described below with reference to the drawings.

First Embodiment

FIGS. 1 to 10 relate to a first embodiment of the present invention.

Figure 1:
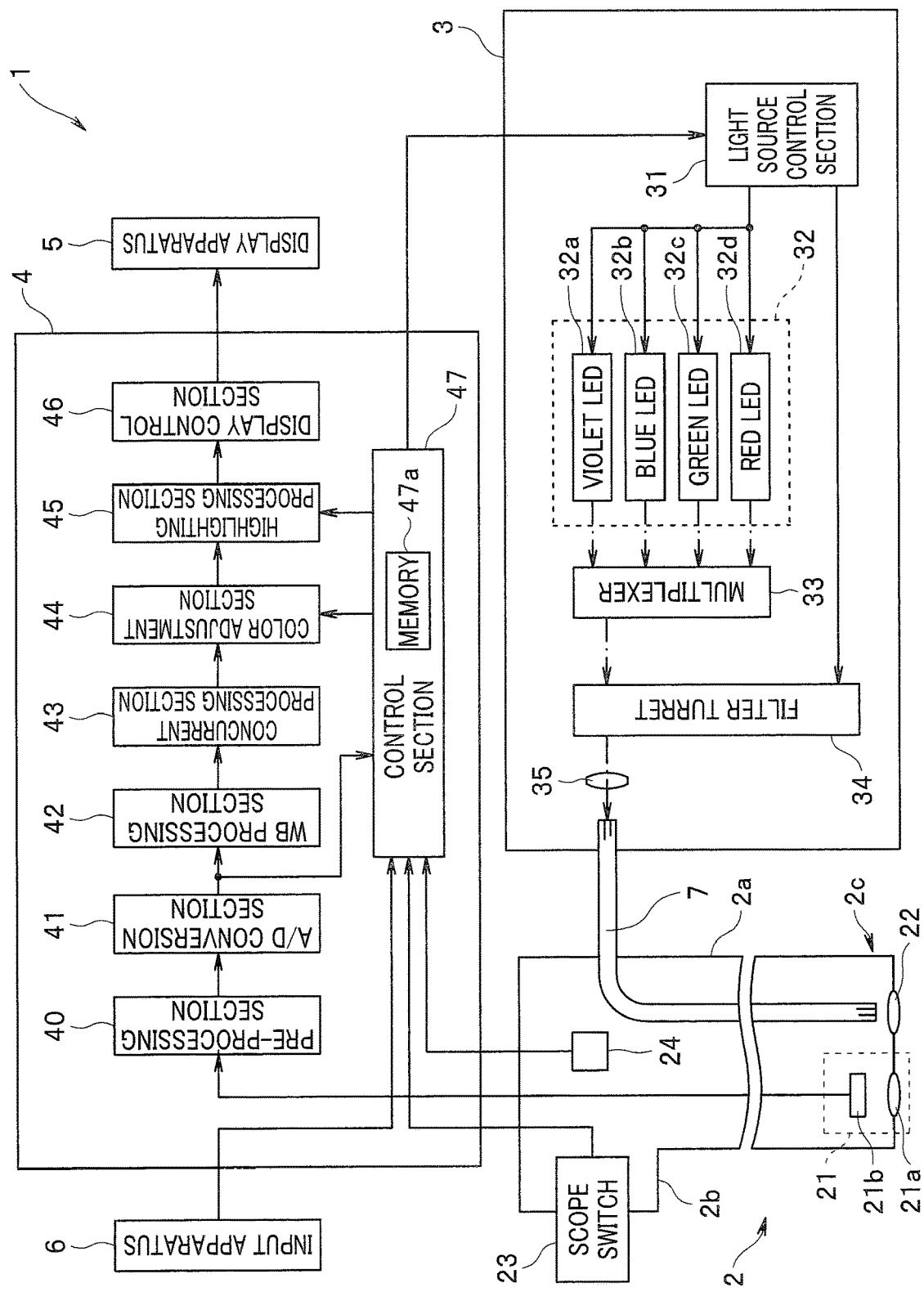
FIG. 1 is a diagram illustrating a configuration of a principal part of an endoscope system according to an embodiment.

An endoscope system 1 includes an endoscope 2 configured to be insertable into a subject while picking up an image of an object such as a living tissue within the subject and output an image pickup signal, a light source apparatus 3 configured to supply illumination light used to observe the subject via a light guide 7 arranged to be inserted into the endoscope 2, a processor 4 configured to generate and output a video signal or the like corresponding to the image pickup signal to be outputted from the endoscope 2, a display apparatus 5 configured to display an observation image or the like corresponding to the video signal to be outputted from the processor 4, and an input apparatus 6 including a switch and/or a button or the like capable of issuing an instruction or the like corresponding to an input operation by a user such as an operator to the processor 4, as illustrated in FIG. 1. FIG. 1 is a diagram illustrating a configuration of a principal part of the endoscope system according to the present embodiment.

The endoscope 2 includes an insertion section 2a formed in an elongated shape to be insertable into the subject and an operation section 2b provided on a proximal end side of the insertion section 2a. The endoscope 2 is configured to be detachably connected to the processor 4 via a universal cable (not illustrated) containing a signal line used to transmit various signals such as an image pickup signal to be outputted from an image pickup section 21, for example. The endoscope 2 is configured to be detachably connected to the light source apparatus 3 via a light guide cable (not illustrated) containing at least a part of the light guide 7.

The image pickup section 21 configured to pick up an image of the object such as the living tissue within the subject, an emission end portion of the light guide 7, and an illumination optical system 22 configured to irradiate the object with illumination light transmitted by the light guide 7 are provided in a distal end portion 2c in the insertion section 2a.

The image pickup section 21 is configured to pick up an image of return light from the object illuminated with the illumination light to be emitted via the illumination optical system 22 and output an image pickup signal. More specifically, the image pickup section 21 includes an objective optical system 21a configured to image-form return light to be emitted from the object and an image pickup device 21b configured to dispose a plurality of pixels for receiving the return light and picking up an image of the received return light in a matrix shape to match an image formation position of the objective optical system 21a.

The image pickup device 21b includes an image sensor such as a CCD or a CMOS, and is configured to pick up an image of return light image-formed by the objective optical system 21a to generate an image pickup signal and output the generated image pickup signal to the processor 4.

The operation section 2b is configured to have such a shape as to be operable by being grasped by the user. The operation section 2b is provided with a scope switch 23 configured to include one or more switches capable of issuing the instruction corresponding to the input operation by the user to the processor 4.

A scope memory 24 storing endoscope information including information representing an ID number or the like specific to the endoscope 2 is provided within the operation section 2b. Note that the endoscope information stored in the scope memory 24 is read out by a control section 47 (described below) in the processor 4 when the endoscope 2 and the processor 4 are electrically connected to each other and power to the processor 4 is turned on.

The light source apparatus 3 is configured to include a light source control section 31, a light source unit 32, a multiplexer 33, a filter turret 34, and a condenser lens 35.

The light source control section 31 is configured to include a control circuit configured to control each of the light source unit 32 and the filter turret 34, for example. The light source control section 31 is configured to control each of LEDs (light emitting diodes) provided in the light source unit 32 in response to an illumination control signal to be outputted from the processor 4. The light source control section 31 is configured to perform control for rotating the filter turret 34 in response to a filter switching signal to be outputted from the processor 4.

The light source unit 32 has a function of a light source section, and is configured to include a violet LED 32a, a blue LED 32b, a green LED 32c, and a red LED 32d. Each of the LEDs in the light source unit 32 is configured to individually emit or quench light under the control of the light source control section 31. Each of the LEDs in the light source unit 32 is configured to emit light in a light emission amount corresponding to the control of the light source control section 31.

The violet LED 32a is configured to generate violet light (hereinafter also referred to as V light) having an intensity in a wavelength band that is not less than a wavelength Wva as a wavelength belonging to a violet range and is not more than a wavelength Wvb as a wavelength belonging to a vicinity of a boundary between the violet range and a blue range. Note that a light emission amount EV of the violet LED 32a is defined as a total light amount obtained by accumulating intensities of lights respectively having wavelengths included in a wavelength band of the V light.

The blue LED 32b is configured to generate blue light (hereinafter also referred to as B light) having an intensity in a wavelength band that is not less than a wavelength Wba as a wavelength belonging to the vicinity of the boundary between the violet range and the blue range and shorter than the wavelength Wvb and is not more than a wavelength Wbb as a wavelength belonging to a vicinity of a boundary between the blue range and a green range. Note that a light emission amount EB of the blue LED 32b is defined as a total light amount obtained by accumulating intensities of lights respectively having wavelengths included in a wavelength band of the B light.

The green LED 32c is configured to generate green light (hereinafter referred to as G light) having an intensity in a wavelength band that is not less than a wavelength Wga as a wavelength belonging to the vicinity of the boundary between the blue range and the green range and shorter than the wavelength Wbb and is not more than a wavelength Wge as a wavelength belonging to a vicinity of a boundary between the green range and a red range. Note that a light emission amount EG of the green LED 32c is defined as a total light amount obtained by accumulating intensities of lights respectively having wavelengths included in a wavelength band of the G light.

The red LED 32d is configured to generate red light (hereinafter referred to as R light) having an intensity in a wavelength band that is not less than a wavelength Wra as a wavelength belonging to the vicinity of the boundary between the green range and the red range and shorter than the wavelength Wge and is not more than a wavelength Wrb as a wavelength belonging to the red range. Note that a light emission amount ER of the red LED 32d is defined as a total light amount obtained by accumulating intensities of lights respectively having wavelengths included in a wavelength band of the R light.

The multiplexer 33 is configured to multiplex and emit the lights to be emitted from the light source unit 32.

Figure 2:
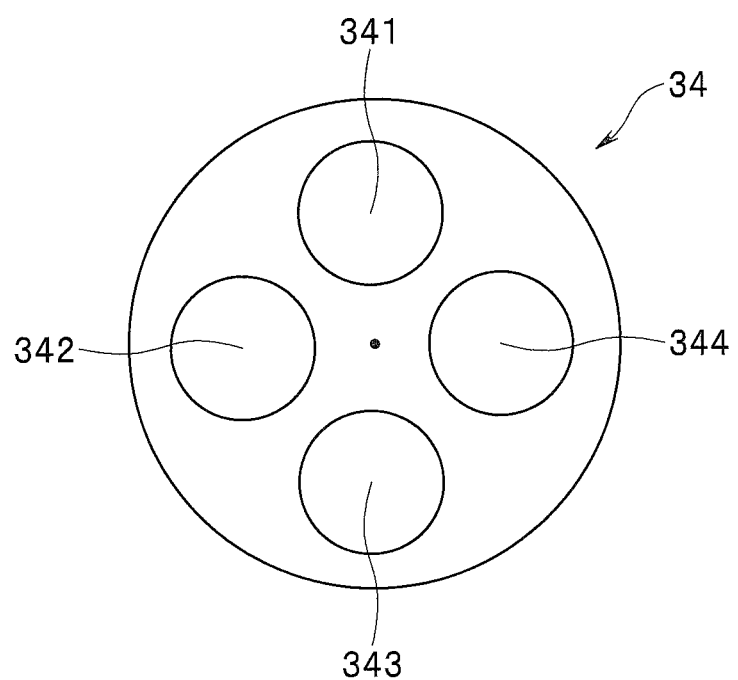
FIG. 2 is a diagram for describing an example of a configuration of a filter turret provided in a light source apparatus according to a first embodiment.

The filter turret 34 is formed to have a disk shape, for example, and is provided to vertically intersect an optical path of light to be emitted via the multiplexer 33. The filter turret 34 is configured by arranging four optical filters 341, 342, 343, and 344 respectively having different spectral transmission characteristics in a circumferential direction, as illustrated in FIG. 2, for example. The filter turret 34 is configured to allow insertion of any one of the optical filters 341, 342, 343, and 344 into an optical path of light to be emitted via the multiplexer 33 by rotating in response to an operation of a motor not illustrated to be controlled by the light source control section 31, for example. FIG. 2 is a diagram for describing an example of a configuration of the filter turret provided in the light source apparatus according to the first embodiment.

Figure 3:
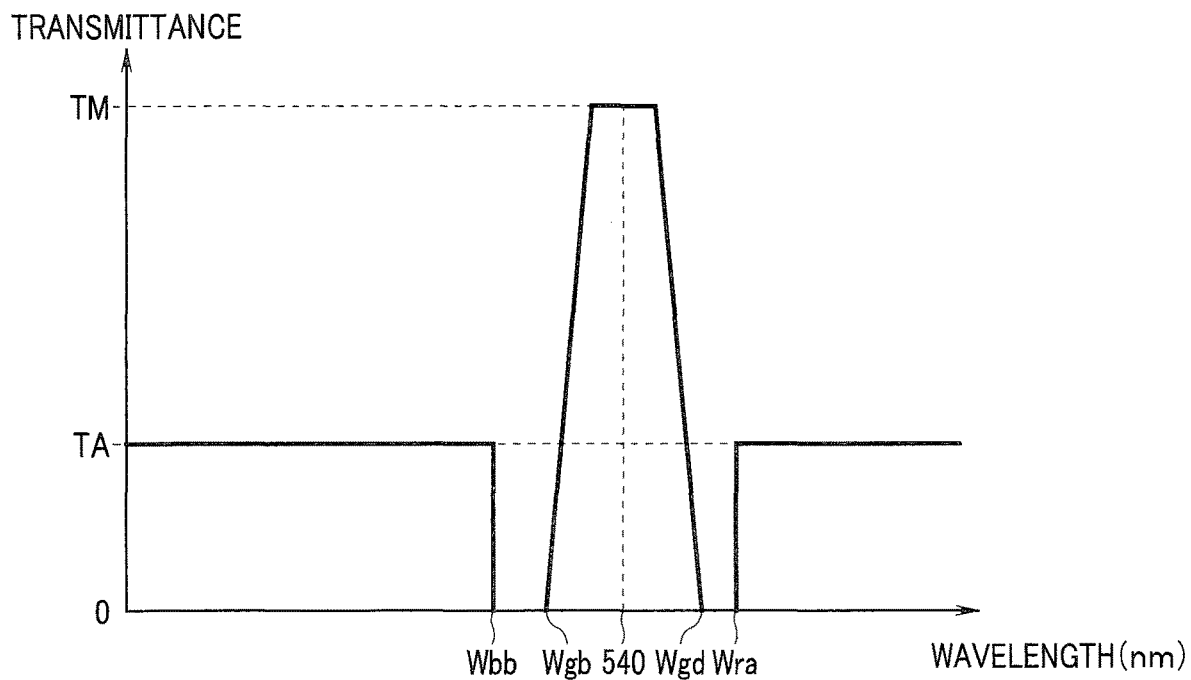
FIG. 3 is a diagram for describing an example of a spectral transmission characteristic of an optical filter provided in the filter turret illustrated in FIG. 2.

The optical filter 341 is configured to have a spectral transmission characteristic to transmit V light and B light each having a wavelength not more than the wavelength Wbb at a transmittance TA, as illustrated in FIG. 3, for example. The optical filter 341 is configured to have a spectral transmission characteristic to transmit R light included in a wavelength band that is not less than the wavelength Wra at the transmittance TA, as illustrated in FIG. 3, for example. The optical filter 341 is configured to have a spectral transmission characteristic to extract from G light to be emitted from the green LED 32c G1 light having an intensity in a wavelength band that is not less than a wavelength Wgb as a wavelength longer than the wavelength Wbb and is not more than a wavelength Wgd as a wavelength shorter than the wavelength Wra while setting 540 nm corresponding to a maximum wavelength of an absorbance by hemoglobin as a central wavelength and transmit the extracted light at a transmittance TM, as illustrated in FIG. 3, for example. FIG. 3 is a diagram for describing an example of the spectral transmission characteristic of the optical filter provided in the filter turret illustrated in FIG. 2.

The transmittance TA is set as a value within a range larger than zero and smaller than the transmittance TM. The transmittance TM is set as a value corresponding to one or substantially one, for example. Note that a setting condition of a value of the transmittance TA will be described below.

In other words, the optical filter 341 is configured to have a spectral transmission characteristic to respectively reduce a light amount of the V light to be emitted from the violet LED 32a, a light amount of the B light to be emitted from the blue LED 32b, and a light amount of the R light to be emitted from the red LED 32d while changing a spectrum of the G light to be emitted from the green LED 32c into a spectrum set to reach an intermediate mucosal layer in a wavelength band having a high absorbance by hemoglobin.

Figure 4:
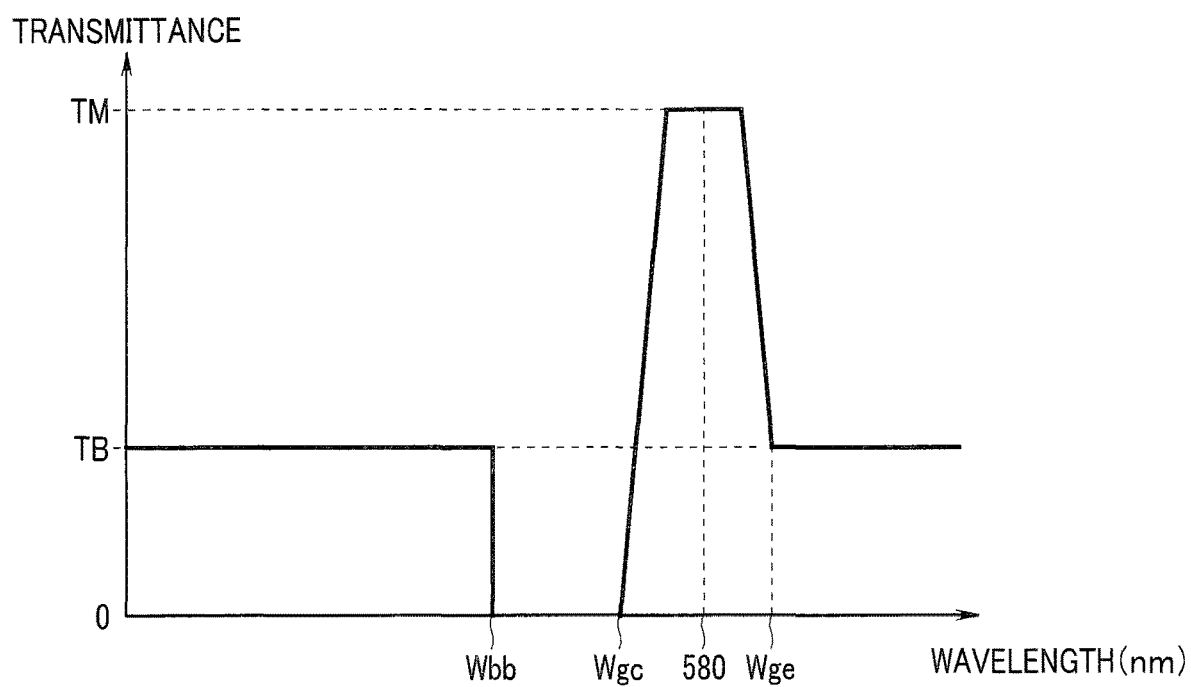
FIG. 4 is a diagram for describing an example of the spectral transmission characteristic of the optical filter provided in the filter turret illustrated in FIG. 2.

The optical filter 342 is configured to have a spectral transmission characteristic to transmit V light and B light each having a wavelength that is not more than the wavelength Wbb at a transmittance TB, as illustrated in FIG. 4, for example. The optical filter 342 is configured to have a spectral transmission characteristic to transmit R light included in a wavelength band that is not less than the wavelength Wge at the transmittance TB, as illustrated in FIG. 4, for example. The optical filter 342 is configured to have a spectral transmission characteristic to extract from G light to be emitted from the green LED 32c G2 light having an intensity in a wavelength band that is not less than a wavelength Wgc as a wavelength belonging between the wavelength Wgb and the wavelength Wgd and is not more than the wavelength Wge while setting 580 nm corresponding to a maximum wavelength of an absorbance by hemoglobin as a central wavelength and transmit the extracted light at the transmittance TM, as illustrated in FIG. 4, for example. In other words, in the present embodiment, a spectrum of the G1 light to be emitted via the optical filter 341 and a spectrum of the G2 light to be emitted via the optical filter 342 overlap each other in a wavelength band that is not less than the wavelength Wgc nor more than the wavelength Wgd. FIG. 4 is a diagram for describing an example of the spectral transmission characteristic of the optical filter provided in the filter turret illustrated in FIG. 2.

The transmittance TB is set as a value within a range larger than zero and smaller than the transmittance TM. Note that a setting condition of the value of the transmittance TB will be described below.

In other words, the optical filter 342 is configured to have a spectral transmission characteristic to respectively reduce a light amount of the V light to be emitted from the violet LED 32a, a light amount of the B light to be emitted from the blue LED 32b, and a light amount of the R light to be emitted from the red LED 32d while changing a spectrum of the G light to be emitted from the green LED 32c into a spectrum set to reach a deep mucosal layer (a layer deeper than the intermediate mucosal layer) in the wavelength band having a high absorbance by hemoglobin.

Figure 5:
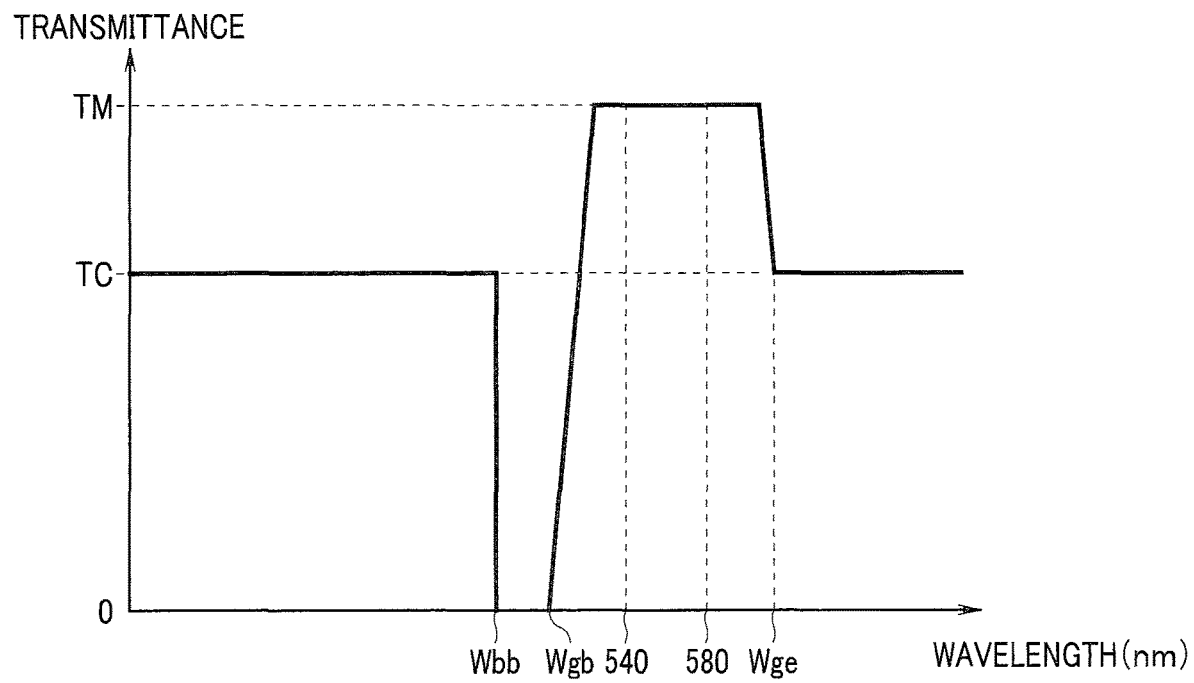
FIG. 5 is a diagram for describing an example of the spectral transmission characteristic of the optical filter provided in the filter turret illustrated in FIG. 2.

The optical filter 343 is configured to have a spectral transmission characteristic to transmit V light and B light each having a wavelength not more than the wavelength Wbb at a transmittance TC, as illustrated in FIG. 5, for example. The optical filter 343 is configured to have a spectral transmission characteristic to transmit R light included in a wavelength band that is not less than the wavelength Wge at the transmittance TC, as illustrated in FIG. 5, for example. The optical filter 343 is configured to have a spectral transmission characteristic to extract from G light to be emitted from the green LED 32c G3 light as light having an intensity in a wavelength band that is not less than the wavelength Wgb nor more than the wavelength Wge while including wavelengths 540 nm and 580 nm corresponding to a maximum wavelength of an absorbance by hemoglobin and transmit the extracted light at the transmittance TM, as illustrated in FIG. 5, for example. FIG. 5 is a diagram for describing an example of the spectral transmission characteristic of the optical filter provided in the filter turret illustrated in FIG. 2.

The transmittance TC is set as a value within a range larger than both the transmittances TA and TB and smaller than the transmittance TM. Note that a setting condition of the value of the transmittance TC will be described below.

In other words, the optical filter 343 is configured to have a spectral transmission characteristic to respectively reduce a light amount of the V light to be emitted from the violet LED 32a, a light amount of the B light to be emitted from the blue LED 32b, and a light amount of the R light to be emitted from the red LED 32d while changing a spectrum of the G light to be emitted from the green LED 32c into a spectrum set to reach two layers, that is, an intermediate mucosal layer and a deep mucosal layer at one time in the wavelength band having a high absorbance by hemoglobin.

Figure 6:
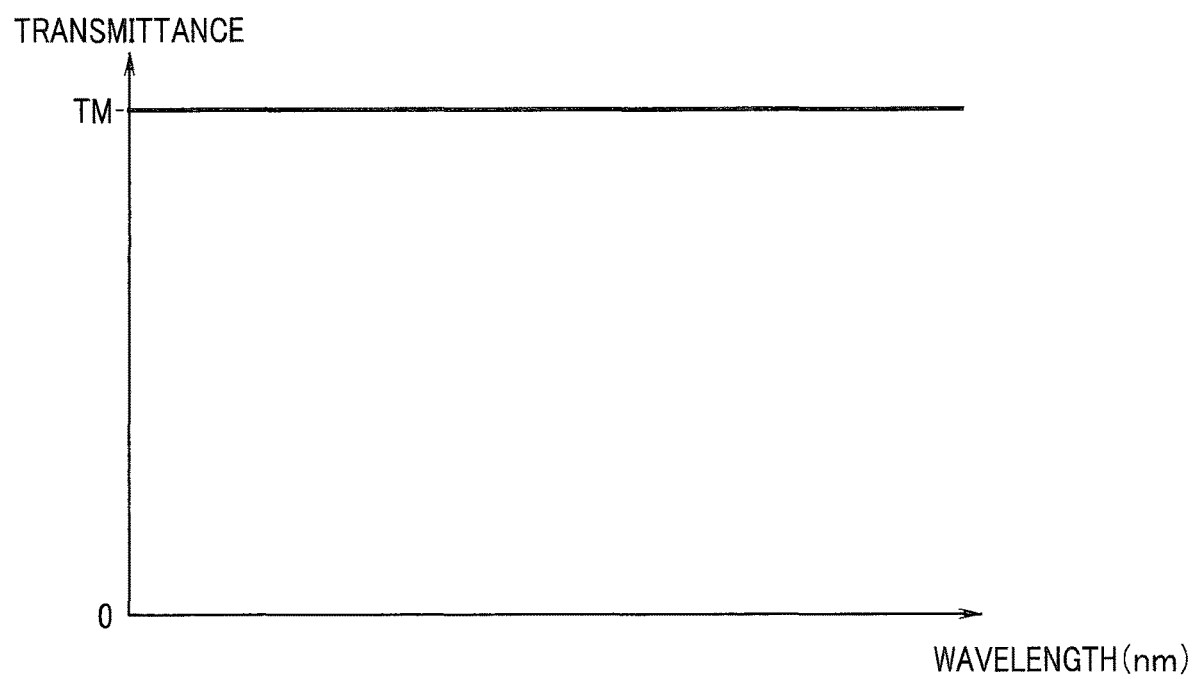
FIG. 6 is a diagram for describing an example of the spectral transmission characteristic of the optical filter provided in the filter turret illustrated in FIG. 2.

The optical filter 344 is configured to have a spectral transmission characteristic to transmit lights in all wavelength bands at the transmittance TM, as illustrated in FIG. 6, for example. FIG. 6 is a diagram for describing an example of the spectral transmission characteristic of the optical filter provided in the filter turret illustrated in FIG. 2.

In other words, the filter turret 34 is configured as a filter switching mechanism obtained by integrating respective functions of a spectrum varying section and a light amount adjustment section.

The condenser lens 35 is configured to condense light to be emitted via the filter turret 34 so that the light is incident on an incidence end portion of the light guide 7.

The processor 4 is configured to include a pre-processing section 40, an A/D conversion section 41, a WB (white balance) processing section 42, a concurrent processing section 43, a color adjustment section 44, a highlighting processing section 45, a display control section 46, and a control section 47. Note that according to the present embodiment, each of the sections in the processor 4 may be configured as an individual electronic circuit, or may be configured as a circuit block in an integrated circuit such as an FPGA (field programmable gate array).

The pre-processing section 40 is configured to include a signal processing circuit, for example. The pre-processing section 40 is configured to subject an image pickup signal to be outputted from the image pickup section 21 in the endoscope 2 to predetermined signal processing such as amplification and noise removal and output the image pickup signal to the A/D conversion section 41.

The A/D conversion section 41 is configured to include an A/D conversion circuit, for example. The A/D conversion section 41 is configured to subject the image pickup signal to be outputted from the pre-processing section 40 to processing such as A/D conversion to generate image data and sequentially output the generated image data to the WB processing section 42 and the control section 47.

The WB processing section 42 is configured to include a white balance processing circuit, for example. The WB processing section 42 is configured to subject the image data to be outputted from the A/D conversion section 41 to white balance processing while outputting the image data, which has been subjected to the white balance processing, to the concurrent processing section 43.

The concurrent processing section 43 is configured to include a concurrent processing circuit, for example. The concurrent processing section 43 is configured to perform concurrent processing for storing image data respectively corresponding to a plurality of color components to be sequentially outputted from the A/D conversion section 41 and concurrently reading out the stored image data while outputting image data obtained by the concurrent processing to the color adjustment section 44.

The color adjustment section 44 is configured to include a color adjustment circuit, for example. The color adjustment section 44 is configured to subject the image data to be outputted from the concurrent processing section 43 to color adjustment processing while outputting the image data, which has been subjected to the color adjustment processing, to the highlighting processing section 45 under the control of the control section 47. Note that details of the color adjustment processing to be performed in the color adjustment section 44 will be described below.

The highlighting processing section 45 is configured to include a highlighting processing circuit, for example. The highlighting processing section 45 is configured to perform highlighting processing for highlighting sharpness of the image data to be outputted from the color adjustment section 44 using a spatial filter while outputting the image data, which has been subjected to the highlighting processing, to the display control section 46 under the control of the control section 47. Details of the highlighting processing to be performed in the highlighting processing section 45 will be described below.

The display control section 46 is configured to include a display control circuit, for example. The display control section 46 is configured to assign the image data to be outputted from the highlighting processing section 45 to an R channel, a G channel, and a B channel of the display apparatus 5 to generate a video signal and output the generated video signal to the display apparatus 5.

The control section 47 is configured to include a control circuit, for example. The control section 47 includes a memory 47a previously storing information such as a plurality of color adjustment coefficients usable for color adjustment processing by the color adjustment section 44 and a plurality of spatial filters usable for highlighting processing by the highlighting processing section 45. The control section 47 is configured to read endoscope information stored in the scope memory 24 when the endoscope 2 and the processor 4 are electrically connected to each other and power to the processor 4 is turned on.

The control section 47 is configured to generate an illumination control signal and a filter switching signal for emitting illumination light corresponding to a desired illumination mode set in an illumination mode changeover switch (not illustrated) provided in the input apparatus 6 and/or the scope switch 23 from the light source apparatus 3 and output the generated illumination control signal and filter switching signal to the light source control section 31 based on an instruction from the illumination mode changeover switch. The control section 47 is configured to generate an illumination control signal for changing a light emission amount of each of the LEDs in the light source unit 32 and output the generated illumination control signal to the light source control section 31 in response to brightness of the image data to be outputted from the A/D conversion section 41.

The control section 47 is configured to read a color adjustment coefficient corresponding to a desired illumination mode set in the illumination mode changeover switch provided in the input apparatus 6 and/or the scope switch 23 from a memory 47a while subjecting the color adjustment section 44 to control for performing color adjustment processing using the read color adjustment coefficient.

The control section 47 is configured to read a spatial filter corresponding to a desired illumination mode set in the illumination mode changeover switch provided in the input apparatus 6 and/or the scope switch 23 from the memory 47*a* while subjecting the highlighting processing section 45 to control for performing highlighting processing using the read spatial filter.

Then, functions of the present embodiment will be described below.

First, the user performs an operation for connecting the sections in the endoscope system 1 to one another to turn on power to the endoscope system 1 and then switching the scope switch 23 and/or an illumination switch (not illustrated) provided in the input apparatus 6 from OFF to ON, for example, to instruct the control section 47 to supply illumination light from the light source apparatus 3 to the endoscope 2. The user operates the scope switch 23 and/or the illumination mode changeover switch provided in the input apparatus 6 to instruct the control section 47 to set an illumination mode of the endoscope system 1 to a first illumination mode.

The control section 47 causes each of the LEDs in the light source unit 32 to emit light in a predetermined light emission amount ratio RT while generating an illumination control signal for causing the LEDs to respectively emit lights by time division in a predetermined order and outputting the generated illumination control signal to the light source control section 31 when the control section 47 detects that the illumination switch has been turned on.

Figure 7:
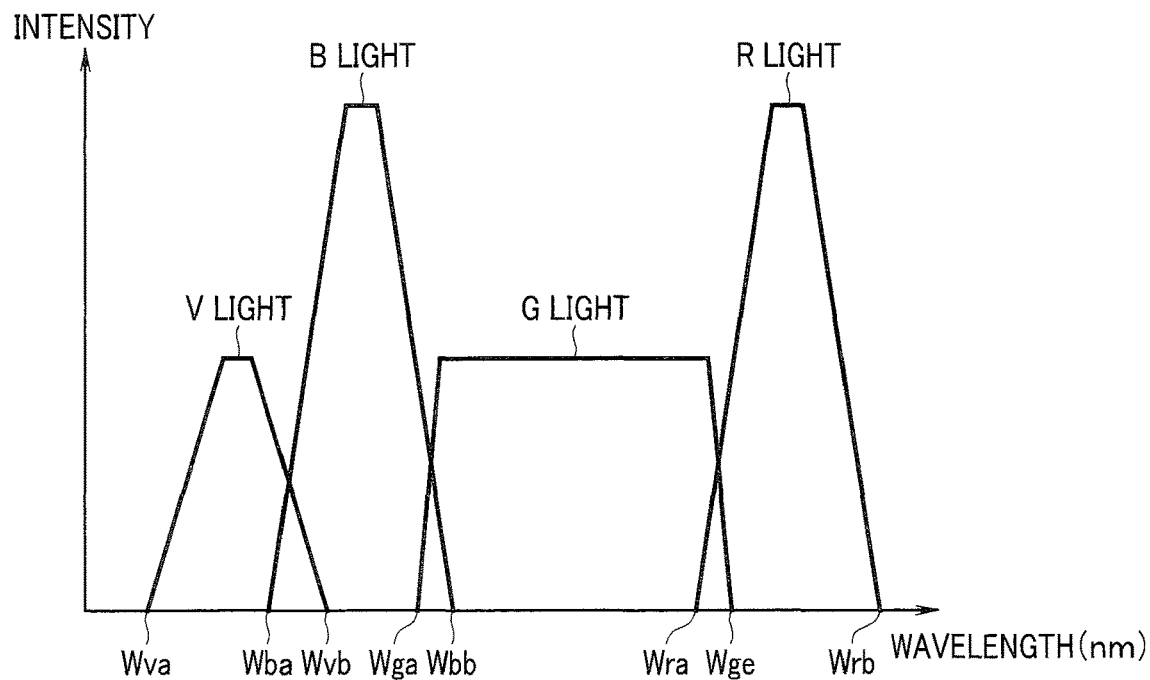
FIG. 7 is a diagram for describing an example of light to be emitted from each of LEDs provided in the light source apparatus according to the first embodiment.

More specifically, the control section 47 causes the LEDs in the light source unit 32 to respectively emit lights in a light emission amount ratio satisfying a relationship expressed by the following equation (1), for example, while generating an illumination control signal for causing the violet LED 32*a* and the blue LED 32*b*, the green LED 32*c*, and the red LED 32*d* to emit lights in this order and outputting the generated illumination control signal to the light source control section 31 when the control section 47 detects that the illumination switch has been turned on. According to such an operation of the control section 47, V light, B light, G light, and R light as illustrated in FIG. 7 are respectively emitted from the LEDs in the light source unit 32, for example. According to such an operation of the control section 47, VB light as mixed light of V light and B light, G light, and R light are sequentially emitted, respectively, from the LEDs in the light source unit 32. Note that α and β in the following equation (1) represent constants respectively set as values satisfying α≥1 and β≤1 based on a spectral characteristic of the entire endoscope system 1, for example. FIG. 7 is a diagram for describing an example of lights respectively emitted from the LEDs provided in the light source apparatus according to the first embodiment.

$$\alpha \times (EV + EB) = EG = \beta \times ER \quad (1)$$

The control section 47 generates a filter switching signal for supplying light, which has passed through the optical filter 341, as illumination light and outputs the generated filter switching signal to the light source control section 31 when the control section 47 detects the instruction to set the illumination mode of the endoscope system 1 to the first illumination mode.

Figure 8:
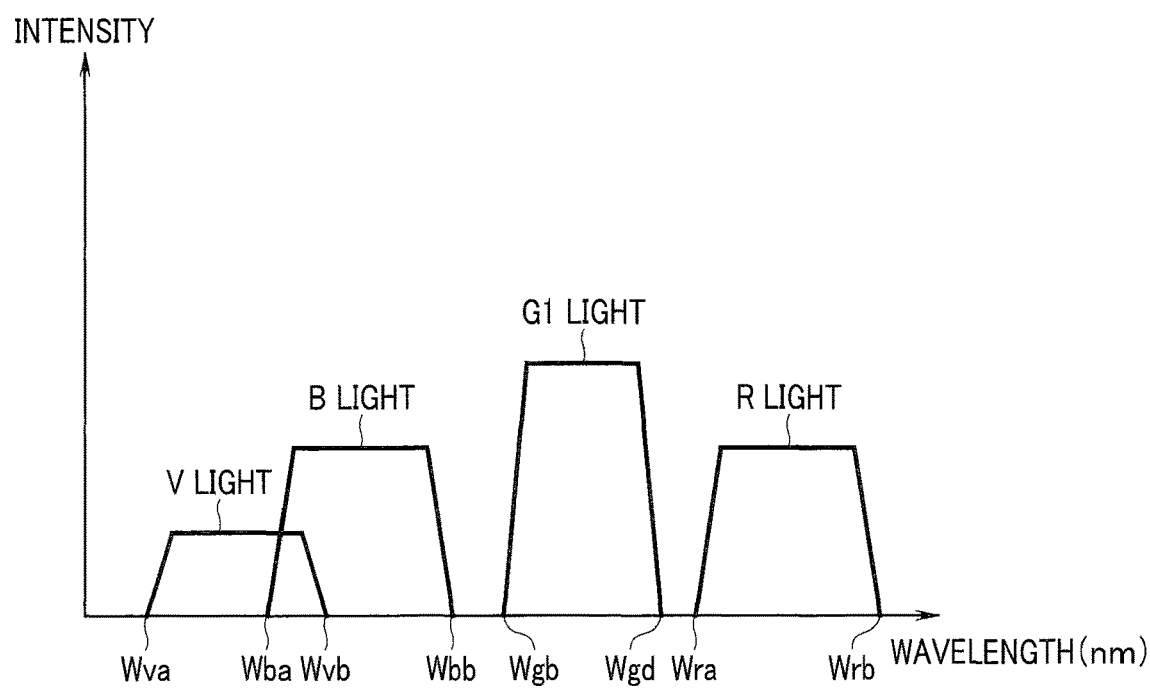
FIG. 8 is a diagram for describing an example of illumination light to be supplied from the light source apparatus in the first embodiment.

The light source control section 31 controls each of the LEDs provided in the light source unit 32 in response to the illumination control signal to be outputted from the control section 47. The light source control section 31 performs control to rotate the filter turret 34 such that the optical filter 341 is inserted into an optical path of light to be emitted via the multiplexer 33 in response to the filter switching signal to be outputted from the control section 47. According to such an operation of the light source control section 31, VB light including V light and B light, G1 light, and R light, as illustrated in FIG. 8, for example, are sequentially supplied as illumination light to the endoscope 2 from the light source apparatus 3. FIG. 8 is a diagram for describing an example of illumination light to be supplied from the light source apparatus in the first embodiment.

If a light amount obtained by accumulating respective intensities of lights having wavelengths included in a wavelength band of G1 light is taken as EG1, light in each of colors to be emitted via the optical filter 341 includes a light emission amount ratio to satisfy a relationship expressed by the following equation (2). Note that in the following equation (2), α1 represents a smaller constant than the constant α, and β1 represents a smaller constant than the constant β.

$$\alpha 1 \times (EV + EB) = EG1 = \beta 1 \times ER \quad (2)$$

In other words, the transmittance TA of the optical filter 341 is set as a value corresponding to a combination of the constants α1 and β1 satisfying the relationship expressed by the foregoing equation (2) within a range larger than zero and smaller than the transmittance TM.

The image pickup section 21 picks up an image of return light from the object illuminated with VB light, G1 light, and R light to be supplied from the light source apparatus 3 to generate an image pickup signal and outputs the generated image pickup signal to the processor 4.

The pre-processing section 40 subjects the image pickup signal to be outputted from the image pickup section 21 to predetermined signal processing such as amplification and noise removal and outputs the image pickup signal to the A/D conversion section 41.

The A/D conversion section 41 subjects the image pickup signal to be outputted from the pre-processing section 40 to processing such as A/D conversion, to generate image data IVB having a violet component and a blue component obtained by image pickup of return light from the object illuminated with VB light, image data IG1 having a green component obtained by image pickup of return light from the object illuminated with G1 light, and image data IR having a red component obtained by image pickup of return light from the object illuminated with R light and sequentially output the image data to the WB processing section 42.

The WB processing section 42 subjects the image data IVB, IG1, and IR to be outputted from the A/D conversion section 41 to white balance processing while outputting each of the image data, which have been subjected to the white balance processing, to the concurrent processing section 43.

The concurrent processing section 43 performs concurrent processing for accumulating the image data IVB, IG1, and IR to be sequentially outputted from the WB processing section 42 and concurrently reading out the image data while outputting the image data obtained by the concurrent processing to the color adjustment section 44.

The control section 47 subjects the color adjustment section 44 to control for reading color adjustment coefficients GainB, GainGA, and GainR from the memory 47*a* while performing color adjustment processing using each of the read color adjustment coefficients when the control section 47 detects the instruction to set the illumination mode of the endoscope system 1 to the first illumination mode.

The color adjustment section 44 performs processing for multiplying the image data IVB to be outputted from the concurrent processing section 43 by the color adjustment coefficient GainB, multiplying the image data IG1 to be outputted from the concurrent processing section 43 by the color adjustment coefficient GainA, and multiplying the image data IR to be outputted from the concurrent processing section 43 by the color adjustment coefficient GainR as color adjustment processing while outputting each of the image data, which have been subjected to the color adjustment processing, to the highlighting processing section 45 under the control of the control section 47.

The control section 47 subjects the highlighting processing section 45 to control for reading spatial filters SFB, SFG, and SFR from the memory 47a while performing highlighting processing using each of the read spatial filters when the control section 47 detects the instruction to set the illumination mode of the endoscope system 1 to the first illumination mode.

Note that the spatial filter SFB is configured as a filter to be highlighted in a maximum highlighting amount in a spatial frequency SB positioned on a higher band side in a section from zero to a Nyquist frequency, for example. The spatial filter SFR is configured as a filter to be highlighted in a maximum highlighting amount in a spatial frequency SR positioned on a lower band side in the section from zero to the Nyquist frequency, for example. The spatial filter SFG is configured as a filter to be highlighted in a maximum highlighting amount in a spatial frequency SG positioned between the spatial frequencies SR and SB in the section from zero to the Nyquist frequency, for example.

The highlighting processing section 45 performs processing for highlighting sharpness of the image data IVB to be outputted from the color adjustment section 44 by the spatial filter SFB, highlighting sharpness of the image data IG1 to be outputted from the color adjustment section 44 by the spatial filter SFG, and highlighting sharpness of the image data IR to be outputted from the color adjustment section 44 by the spatial filter SFR as highlighting processing while outputting each of the image data, which have been subjected to the highlighting processing, to the display control section 46 under the control of the control section 47.

The display control section 46 assigns the image data IVB to be outputted from the highlighting processing section 45 to the B channel of the display apparatus 5, assigns the image data IG1 to be outputted from the highlighting processing section 45 to the G channel of the display apparatus 5, and assigns the image data IR to be outputted from the highlighting processing section 45 to the R channel of the display apparatus 5 to generate a video signal, and outputs the generated video signal to the display apparatus 5.

According to the operation as described above, when the illumination mode of the endoscope system 1 is set to the first illumination mode, the respective light amounts of the V light, the B light, and the R light to be supplied to the endoscope 2 from the light source apparatus 3 are adjusted with the light amount EG1 of the G1 light as a reference. According to the operation as described above, when the illumination mode of the endoscope system 1 is set to the first illumination mode, the object is irradiated with illumination light including the G1 light that reaches an intermediate mucosal layer in a deep portion of a mucous membrane of the living tissue and has a high absorbance by hemoglobin while the image data IG1 obtained by image pickup of return light from the object illuminated with the G1 light is subjected to color adjustment processing and highlighting processing. Accordingly, according to the operation as described above, when the illumination mode of the endoscope system 1 is set to the first illumination mode, an observation image having a color tone suitable for observation of the intermediate mucosal layer of the living tissue and faithfully reproducing a distribution of hemoglobin in the intermediate mucosal layer can be displayed on the display apparatus 5.

The user operates the scope switch 23 and/or the illumination mode changeover switch provided in the input apparatus 6, to instruct the control section 47 to set the illumination mode of the endoscope system 1 to a second illumination mode.

The control section 47 generates a filter switching signal for supplying light, which has passed through the optical filter 342, as illumination light and outputs the generated filter switching signal to the light source control section 31 when the control section 47 detects the instruction to set the illumination mode of the endoscope system 1 to the second illumination mode.

Figure 9:
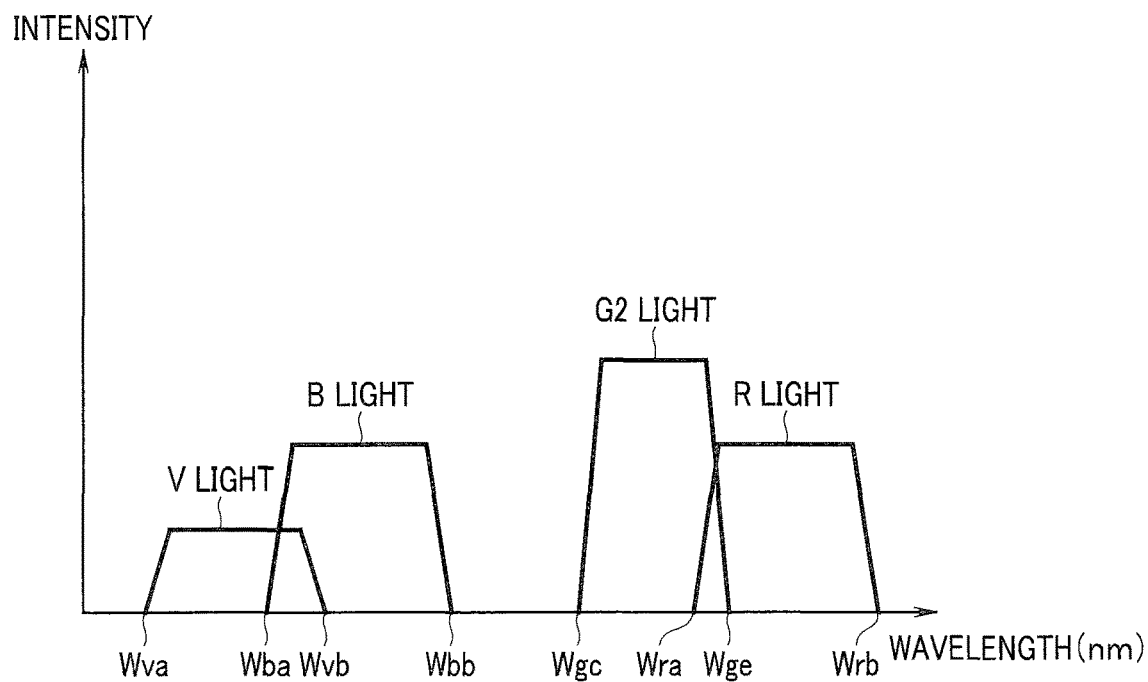
FIG. 9 is a diagram for describing an example of illumination light to be supplied from the light source apparatus in the first embodiment.

The light source control section 31 performs control to rotate the filter turret 34 such that the optical filter 342 is inserted into an optical path of light to be emitted via the multiplexer 33 in response to the filter switching signal to be outputted from the control section 47. According to such an operation of the light source control section 31, VB light including V light and B light, G2 light, and R light, as illustrated in FIG. 9, for example, are sequentially supplied as illumination light to the endoscope 2 from the light source apparatus 3. FIG. 9 is a diagram for describing an example of illumination light to be supplied from the light source apparatus in the first embodiment.

If a light amount obtained by accumulating intensities of lights having wavelengths included in a wavelength band of the G2 light is taken as EG2, light in each of colors to be emitted via the optical filter 342 includes a light emission amount ratio to satisfy a relationship expressed by the following equation (3). Note that in the following equation (3), α2 represents a smaller constant than the constant α, and β2 represents a smaller constant than the constant β.

$$\alpha 2 \times (EV + EB) = EG2 = \beta 2 \times ER \quad (3)$$

In other words, the transmittance TB of the optical filter 342 is set as a value corresponding to a combination of the constants α2 and β2 satisfying the relationship expressed by the foregoing equation (3) within a range larger than zero and smaller than the transmittance TM.

The image pickup section 21 picks up an image of return light from the object illuminated with the VB light, the G2 light, and the R light to be supplied from the light source apparatus 3 to generate an image pickup signal and outputs the generated image pickup signal to the processor 4.

The pre-processing section 40 subjects the image pickup signal to be outputted from the image pickup section 21 to predetermined signal processing such as amplification and noise removal and outputs the image pickup signal to the A/D conversion section 41.

The A/D conversion section 41 subjects the image pickup signal to be outputted from the pre-processing section 40 to processing such as A/D conversion, to generate the image data IVB, image data IG2 having a green component obtained by image pickup of return light from the object illuminated with the G2 light, and the image data IR and sequentially output the image data to the WB processing section 42.

The WB processing section 42 subjects the image data IVB, IG2, and IR to be outputted from the A/D conversion section 41 to white balance processing while outputting each of the image data, which have been subjected to the white balance processing, to the concurrent processing section 43.

The concurrent processing section 43 performs concurrent processing for accumulating the image data IVB, IG2, and IR to be sequentially outputted from the WB processing section 42 and concurrently reading out the image data while outputting the image data obtained by the concurrent processing to the color adjustment section 44.

The control section 47 subjects the color adjustment section 44 to control for reading color adjustment coefficients GainB, GainGB, and GainR from the memory 47a while performing color adjustment processing using each of the read color adjustment coefficients when the control section 47 detects the instruction to set the illumination mode of the endoscope system 1 to the second illumination mode. Note that the color adjustment coefficient GainGB is set to the same value as the color adjustment coefficient GainGA, for example.

The color adjustment section 44 performs processing for multiplying the image data IVB to be outputted from the concurrent processing section 43 by the color adjustment coefficient GainB, multiplying the image data IG2 to be outputted from the concurrent processing section 43 by the color adjustment coefficient GainGB, and multiplying the image data IR to be outputted from the concurrent processing section 43 by the color adjustment coefficient GainR as color adjustment processing while outputting each of the image data, which have been subjected to the color adjustment processing, to the highlighting processing section 45 under the control of the control section 47.

The control section 47 subjects the highlighting processing section 45 to control for reading the spatial filters SFB, SFG, and SFR from the memory 47a while performing highlighting processing using each of the read spatial filters when the control section 47 detects the instruction to set the illumination mode of the endoscope system 1 to the second illumination mode.

The highlighting processing section 45 performs processing for highlighting sharpness of the image data IVB to be outputted from the color adjustment section 44 by the spatial filter SFB, highlighting sharpness of the image data IG2 to be outputted from the color adjustment section 44 by the spatial filter SFG, and highlighting sharpness of the image data IR to be outputted from the color adjustment section 44 by the spatial filter SFR as highlighting processing while outputting each of the image data, which have been subjected to the highlighting processing, to the display control section 46 under the control of the control section 47.

The display control section 46 assigns the image data IVB to be outputted from the highlighting processing section 45 to the B channel of the display apparatus 5, assigns the image data IG2 to be outputted from the highlighting processing section 45 to the G channel of the display apparatus 5, and assigns the image data IR to be outputted from the highlighting processing section 45 to the R channel of the display apparatus 5 to generate a video signal, and outputs the generated video signal to the display apparatus 5.

According to the operation as described above, when the illumination mode of the endoscope system 1 is set to the second illumination mode, the respective light amounts of the V light, the B light, and the R light to be supplied to the endoscope 2 from the light source apparatus 3 are adjusted with the light amount EG2 of the G2 light as a reference. According to the operation as described above, when the illumination mode of the endoscope system 1 is set to the second illumination mode, the object is irradiated with illumination light including the G2 light that reaches a deep mucosal layer as a layer deeper than the intermediate mucosal layer in the deep portion of the mucous membrane of the living tissue and has a high absorbance by hemoglobin while the image data IG2 obtained by image pickup of return light from the object illuminated with the G2 light is subjected to color adjustment processing and highlighting processing. Accordingly, according to the operation as described above, when the illumination mode of the endoscope system 1 is set to the second illumination mode, an observation image having a color tone suitable for observation of the deep mucosal layer of the living tissue and faithfully reproducing a distribution of hemoglobin in the deep mucosal layer can be displayed on the display apparatus 5.

The user operates the scope switch 23 and/or the illumination mode changeover switch provided in the input apparatus 6, to instruct the control section 47 to set the illumination mode of the endoscope system 1 to a third illumination mode.

The control section 47 generates a filter switching signal for supplying light, which has passed through the optical filter 343, as illumination light and outputs the generated filter switching signal to the light source control section 31 when the control section 47 detects the instruction to set the illumination mode of the endoscope system 1 to the third illumination mode.

Figure 10:
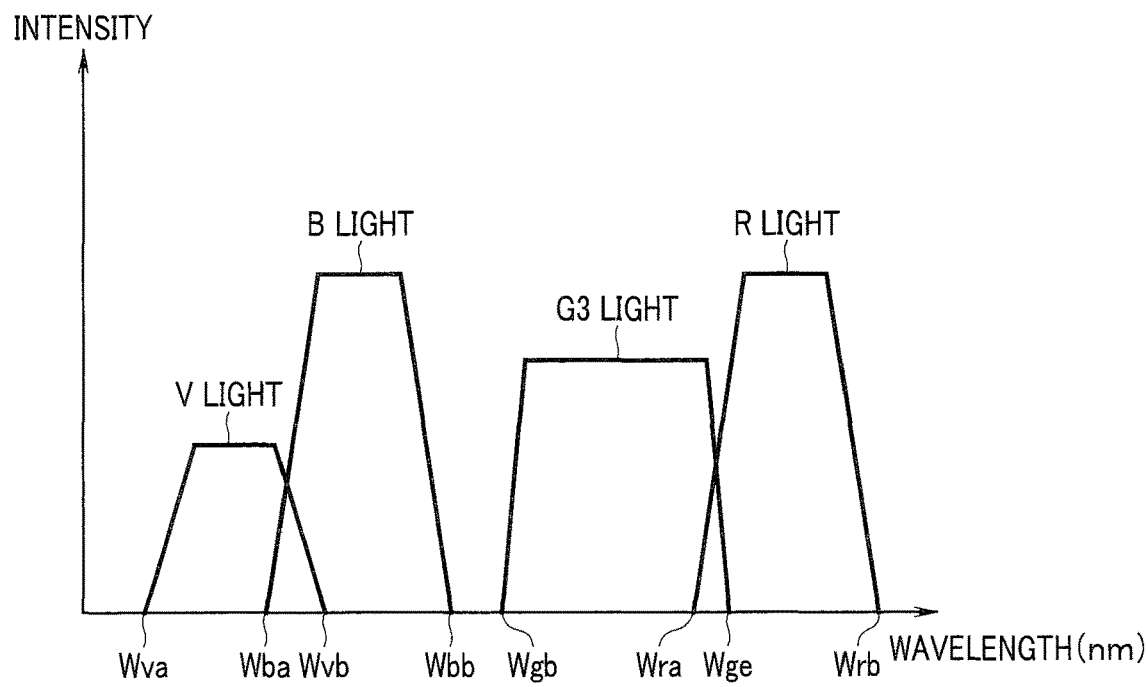
FIG. 10 is a diagram for describing an example of illumination light to be supplied from the light source apparatus in the first embodiment.

The light source control section 31 performs control to rotate the filter turret 34 such that the optical filter 343 is inserted into an optical path of light to be emitted via the multiplexer 33 in response to the filter switching signal to be outputted from the control section 47. According to such an operation of the light source control section 31, VB light including V light and B light, G3 light, and R light, as illustrated in FIG. 10, for example, are sequentially supplied as illumination light to the endoscope 2 from the light source apparatus 3. FIG. 10 is a diagram for describing an example of illumination light to be supplied from the light source apparatus in the first embodiment.

If a light amount obtained by accumulating intensities of lights having wavelengths included in a wavelength band of the G3 light is taken as EG3, light in each of colors to be emitted via the optical filter 343 includes a light emission amount ratio to satisfy a relationship expressed by the following equation (4). Note that in the following equation (4), α3 represents a constant smaller than the constant α and larger than both the constants α1 and α2, and β3 represents a constant smaller than the constant β and larger than both the constants β1 and β2.

$$\alpha 3\times(EV+EB)=EG3=\beta 3\times ER \tag{4}$$

In other words, the transmittance TC of the optical filter 343 is set as a value corresponding to a combination of the constants α3 and β3 satisfying the relationship expressed by the foregoing equation (4) within a range larger than both the transmittances TA and TB and smaller than the transmittance TM.

The image pickup section 21 picks up an image of return light from the object illuminated with the VB light, the G3 light, and the R light to be supplied from the light source apparatus 3 to generate an image pickup signal and outputs the generated image pickup signal to the processor 4.

The pre-processing section 40 subjects the image pickup signal to be outputted from the image pickup section 21 to predetermined signal processing such as amplification and noise removal and outputs the image pickup signal to the A/D conversion section 41.

The A/D conversion section 41 subjects the image pickup signal to be outputted from the pre-processing section 40 to processing such as A/D conversion, to generate the image data IVB, image data IG3 having a green component obtained by image pickup of return light from the object illuminated with the G3 light, and the image data IR and sequentially output the image data to the WB processing section 42.

The WB processing section 42 subjects the image data IVB, IG3, and IR to be outputted from the A/D conversion section 41 to white balance processing while outputting each of the image data, which have been subjected to the white balance processing, to the concurrent processing section 43.

The concurrent processing section 43 performs concurrent processing for accumulating the image data IVB, IG3, and IR to be sequentially outputted from the WB processing section 42 and concurrently reading out the image data while outputting the image data obtained by the concurrent processing to the color adjustment section 44.

The control section 47 subjects the color adjustment section 44 to control for reading color adjustment coefficients GainB, GainGC, and GainR from the memory 47a while performing color adjustment processing using each of the read color adjustment coefficients when the control section 47 detects the instruction to set the illumination mode of the endoscope system 1 to the third illumination mode. Note that the color adjustment coefficient GainGC is set to a value smaller than both the color adjustment coefficients GainGA and GainGB, for example.

The color adjustment section 44 performs processing for multiplying the image data IVB to be outputted from the concurrent processing section 43 by the color adjustment coefficient GainB, multiplying the image data IG3 to be outputted from the concurrent processing section 43 by the color adjustment coefficient GainGC, and multiplying the image data IR to be outputted from the concurrent processing section 43 by the color adjustment coefficient GainR as color adjustment processing while outputting each of the image data, which have been subjected to the color adjustment processing, to the highlighting processing section 45 under the control of the control section 47.

The control section 47 subjects the highlighting processing section 45 to control for reading the spatial filters SFB, SFG, and SFR from the memory 47a while performing highlighting processing using each of the read spatial filters when the control section 47 detects the instruction to set the illumination mode of the endoscope system 1 to the third illumination mode.

The highlighting processing section 45 performs processing for highlighting sharpness of the image data IVB to be outputted from the color adjustment section 44 by the spatial filter SFB, highlighting sharpness of the image data IG3 to be outputted from the color adjustment section 44 by the spatial filter SFG, and highlighting sharpness of the image data IR to be outputted from the color adjustment section 44 by the spatial filter SFR as highlighting processing while outputting each of the image data, which have been subjected to the highlighting processing, to the display control section 46 under the control of the control section 47. The highlighting processing section 45 outputs the image data IV, IB, and IR to be outputted from the color adjustment section 44 to the display control section 46 without subjecting the image data to highlighting processing.

The display control section 46 assigns the image data IVB to be outputted from the highlighting processing section 45 to the B channel of the display apparatus 5, assigns the image data IG3 to be outputted from the highlighting processing section 45 to the G channel of the display apparatus 5, and assigns the image data IR to be outputted from the highlighting processing section 45 to the R channel of the display apparatus 5 to generate a video signal, and outputs the generated video signal to the display apparatus 5.

According to the operation as described above, when the illumination mode of the endoscope system 1 is set to the third illumination mode, the respective light amounts of the V light, the B light, and the R light to be supplied to the endoscope 2 from the light source apparatus 3 are adjusted with the light amount EG3 of the G3 light as a reference. According to the operation as described above, when the illumination mode of the endoscope system 1 is set to the third illumination mode, the object is irradiated with illumination light including the G3 light that reaches two layers, that is, the intermediate mucosal layer and the deep mucosal layer of the living tissue at one time while the image data IG3 obtained by image pickup of return light from the object illuminated with the G3 light is subjected to color adjustment processing and highlighting processing. Accordingly, according to the operation as described above, when the illumination mode of the endoscope system 1 is set to the third illumination mode, an observation image having a color tone suitable for observation of a section from the intermediate mucosal layer to the deep mucosal layer of the living tissue can be displayed on the display apparatus 5.

The user operates the scope switch 23 and/or the illumination mode changeover switch provided in the input apparatus 6, to instruct the control section 47 to set the illumination mode of the endoscope system 1 to a fourth illumination mode.

The control section 47 generates a filter switching signal for supplying light, which has passed through the optical filter 34d, as illumination light and outputs the generated filter switching signal to the light source control section 31 when the control section 47 detects the instruction to set the illumination mode of the endoscope system 1 to the fourth illumination mode.

The light source control section 31 performs control to rotate the filter turret 34 such that the optical filter 34d is inserted into an optical path of light to be emitted via the multiplexer 33 in response to the filter switching signal to be outputted from the control section 47. According to such an operation of the light source control section 31, VB light including V light and B light, G light, and R light, as illustrated in FIG. 7, for example, are sequentially supplied as illumination light to the endoscope 2 from the light source apparatus 3.

The image pickup section 21 picks up an image of return light from the object illuminated with the VB light, the G light, and the R light to be supplied from the light source apparatus 3 to generate an image pickup signal and outputs the generated image pickup signal to the processor 4.

The pre-processing section 40 subjects the image pickup signal to be outputted from the image pickup section 21 to predetermined signal processing such as amplification and noise removal and outputs the image pickup signal to the A/D conversion section 41.

The A/D conversion section 41 subjects the image pickup signal to be outputted from the pre-processing section 40 to processing such as A/D conversion, to generate the image data IVB, image data IG having a green component obtained by image pickup of return light from the object illuminated with the G light, and the image data IR and sequentially output the image data to the WB processing section 42.

The WB processing section 42 subjects the image data IVB, IG, and IR to be outputted from the A/D conversion section 41 to white balance processing while outputting each of the image data, which have been subjected to the white balance processing, to the concurrent processing section 43.

The concurrent processing section 43 performs concurrent processing for accumulating the image data IVB, IG, and IR to be sequentially outputted from the WB processing section 42 and concurrently reading out the image data while outputting the image data obtained by the concurrent processing to the color adjustment section 44.

The control section 47 subjects the color adjustment section 44 to control for reading color adjustment coefficients GainB, GainGD, and GainR from the memory 47a while performing color adjustment processing using each of the read color adjustment coefficients when the control section 47 detects the instruction to set the illumination mode of the endoscope system 1 to the fourth illumination mode. Note that the color adjustment coefficient GainGD is set to a value smaller than the color adjustment coefficient GainGC, for example.

The color adjustment section 44 performs processing for multiplying the image data IVB to be outputted from the concurrent processing section 43 by the color adjustment coefficient GainB, multiplying the image data IG to be outputted from the concurrent processing section 43 by the color adjustment coefficient GainGD, and multiplying the image data IR to be outputted from the concurrent processing section 43 by the color adjustment coefficient GainR as color adjustment processing while outputting each of the image data, which have been subjected to the color adjustment processing, to the highlighting processing section 45 under the control of the control section 47.

The control section 47 subjects the highlighting processing section 45 to control for reading the spatial filters SFB, SFG, and SFR from the memory 47a while performing highlighting processing using each of the read spatial filters when the control section 47 detects the instruction to set the illumination mode of the endoscope system 1 to the fourth illumination mode.

The highlighting processing section 45 performs processing for highlighting sharpness of the image data IVB to be outputted from the color adjustment section 44 by the spatial filter SFB, highlighting sharpness of the image data IG to be outputted from the color adjustment section 44 by the spatial filter SFG, and highlighting sharpness of the image data IR to be outputted from the color adjustment section 44 by the spatial filter SFR as highlighting processing while outputting each of the image data, which have been subjected to the highlighting processing, to the display control section 46 under the control of the control section 47.

The display control section 46 assigns the image data IVB to be outputted from the highlighting processing section 45 to the B channel of the display apparatus 5, assigns the image data IG to be outputted from the highlighting processing section 45 to the G channel of the display apparatus 5, and assigns the image data IR to be outputted from the highlighting processing section 45 to the R channel of the display apparatus 5 to generate a video signal, and outputs the generated video signal to the display apparatus 5.

According to the operation as described above, when the illumination mode of the endoscope system 1 is set to the fourth illumination mode, the object is irradiated with illumination light having a light emission amount ratio to satisfy the relationship expressed by the foregoing equation (1) while an observation image corresponding to return light from the object illuminated with the illumination light can be displayed on the display apparatus 5. Accordingly, according to the operation as described above, when the illumination mode of the endoscope system 1 is set to the fourth illumination mode, an observation image having a color tone in which a region labeled by dispersing pigments on the living tissue and another region are distinguishable, for example, can be displayed on the display apparatus 5.

As described above, according to the present embodiment, an image having a color tone suitable for diagnosis of a lesion existing at a desired depth in the deep portion of the mucous membrane of the living tissue can be acquired.

Note that according to the present embodiment, the LEDs in the light source unit 32 may be caused to concurrently emit lights when a primary color filter that disperses return light incident from the objective optical system 21a into lights in three colors, that is, a red color, a green color, and a blue color is provided on an image pickup surface of the image pickup device 21b, for example.

According to the present embodiment, when the above-described primary color filter is provided on the image pickup surface of the image pickup device 21b, for example, the light source unit 32 may be configured by providing one LED configured to generate broadband light including lights in four colors, that is, V light, B light, G light, and R light instead of the four LEDs that respectively generate the lights in the four colors.

In the present embodiment, respective magnitudes of the light amounts EG1 and EG2 may be made the same by setting the respective transmittances TM of the optical filters 341 and 342 to the same value, for example.

In the present embodiment, the respective magnitudes of the light amounts EG1 and EG2 may be made different from each other by setting the respective transmittances TM of the optical filters 341 and 342 to different values.

According to the present embodiment, highlighting processing as described in Japanese Patent No. 3228627, for example, may be performed in the color adjustment section 44. More specifically, according to the present embodiment, processing for calculating an amount of hemoglobin for each of pixels composing each of the image data to be outputted from the concurrent processing section 43 and highlighting a color of the image data depending on the calculated amount of hemoglobin, for example, may be performed in the color adjustment section 44.

Second Embodiment

FIGS. 11 to 17 relate to a second embodiment of the present invention.

Note that in the present embodiment, a detailed description about sections each having a similar configuration or the like as the configuration or the like in the first embodiment is omitted while sections each having a different configuration or the like from the configuration or the like in the first embodiment will be mainly described.

Figure 11:
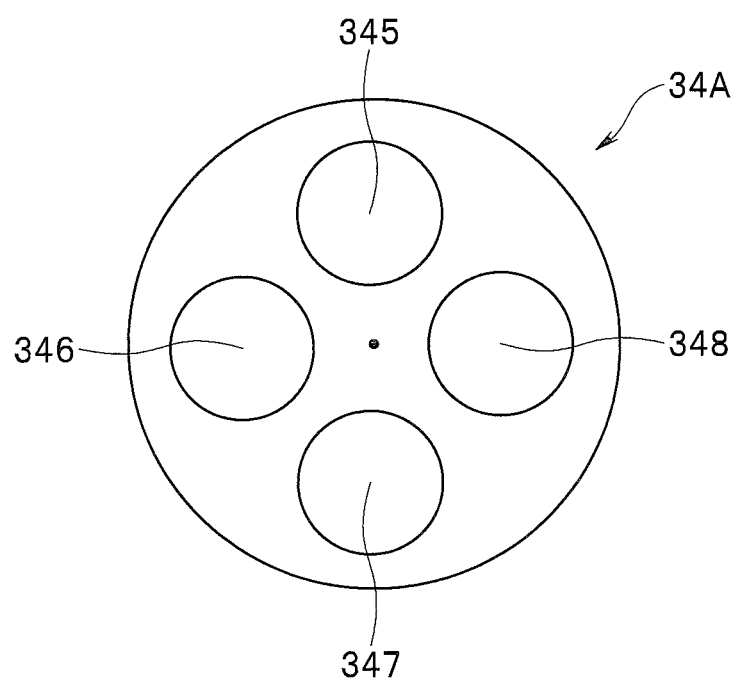
FIG. 11 is a diagram for describing an example of a configuration of a filter turret provided in a light source apparatus according to a second embodiment.

An endoscope system 1 according to the present embodiment is configured by providing a filter turret 34A as illustrated in FIG. 11 in an optical apparatus 3 instead of the filter turret 34. FIG. 11 is a diagram for describing an example of a configuration of the filter turret provided in a light source apparatus according to the second embodiment.

The filter turret 34A is formed to have a disk shape, for example, and is provided to vertically cross an optical path of light to be emitted via a multiplexer 33. The filter turret 34A is configured to arrange four optical filters 345, 346, 347, and 348 respectively having different spectral transmission characteristics in a circumferential direction, as illustrated in FIG. 11, for example. The filter turret 34A is configured to allow insertion of any one of the optical filters 345, 346, 347, and 348 into the optical path of the light to be emitted via the multiplexer 33 by rotating in response to an operation of a motor not illustrated to be controlled by the light source control section 31, for example.

Figure 12:
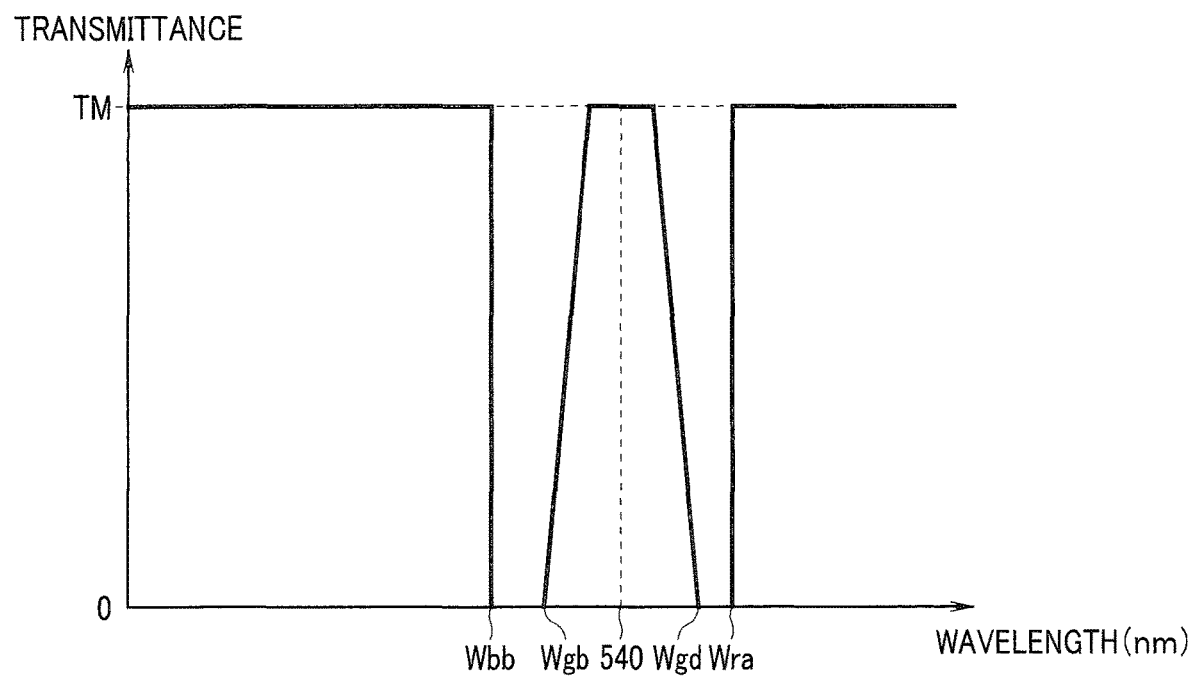
FIG. 12 is a diagram for describing an example of a spectral transmission characteristic of an optical filter provided in the filter turret illustrated in FIG. 11.

The optical filter 345 is configured to have a spectral transmission characteristic to transmit V light and B light each having a wavelength Wbb or less at a transmittance TM, as illustrated in FIG. 12, for example. The optical filter 345 is configured to have a spectral transmission characteristic to transmit R light included in a wavelength band that is not less than a wavelength Wra at the transmittance TM, as illustrated in FIG. 12, for example. The optical filter 345 is configured to have a spectral transmission characteristic to extract from G light to be emitted from a green LED 32c G1 light having an intensity in a wavelength band that is not less than a wavelength Wgb nor more than a wavelength Wgd while setting 540 nm corresponding to a maximum wavelength of an absorbance by hemoglobin as a central wavelength and transmit the extracted light at the transmittance TM, as illustrated in FIG. 12, for example. FIG. 12 is a diagram for describing an example of the spectral transmission characteristic of the optical filter provided in the filter turret illustrated in FIG. 11.

In other words, the optical filter 345 is configured to have a spectral transmission characteristic to change a spectrum of the G light to be emitted from the green LED 32c into a spectrum set to reach an intermediate mucosal layer in the wavelength band having a high absorbance by hemoglobin.

Figure 13:
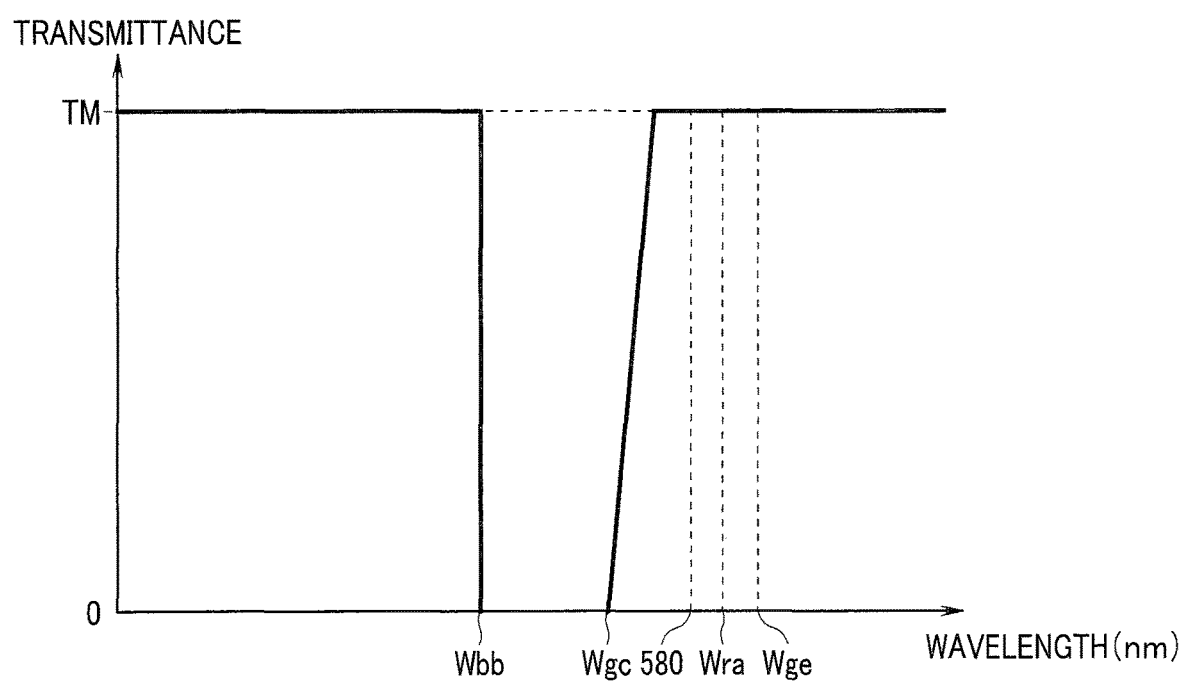
FIG. 13 is a diagram for describing an example of the spectral transmission characteristic of the optical filter provided in the filter turret illustrated in FIG. 11.

The optical filter 346 is configured to have a spectral transmission characteristic to transmit V light and B light each having a wavelength Wbb or less at the transmittance TM, as illustrated in FIG. 13, for example. The optical filter 346 is configured to have a spectral transmission characteristic to have a transmittance larger than zero in a wavelength band that is not less than a wavelength Wgc, as illustrated in FIG. 13, for example. The optical filter 346 is configured to have a spectral transmission characteristic to transmit R light having a wavelength Wra or more at the transmittance TM, as illustrated in FIG. 13. The optical filter 346 is configured to have a spectral transmission characteristic to extract from G light to be emitted from the green LED 32c G2 light having an intensity in a wavelength band that is not less than the wavelength Wgc nor more than a wavelength Wge while setting 580 nm corresponding to a maximum wavelength of an absorbance by hemoglobin as a central wavelength and transmit the extracted light at the transmittance TM, as illustrated in FIG. 13. FIG. 13 is a diagram for describing an example of the spectral transmission characteristic of the optical filter provided in the filter turret illustrated in FIG. 11.

In other words, the optical filter 346 is configured to have a spectral transmission characteristic to change a spectrum of the G light to be emitted from the green LED 32c into a spectrum set to reach a deep mucosal layer in the wavelength band having a high absorbance by hemoglobin.

Figure 14:
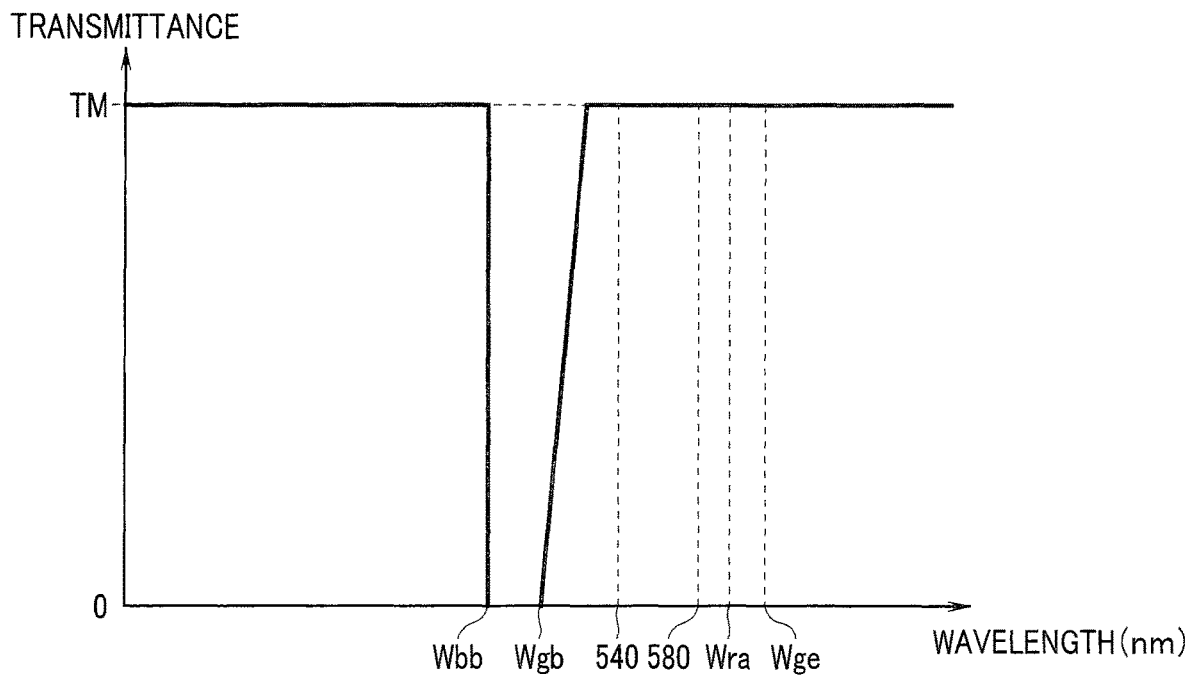
FIG. 14 is a diagram for describing an example of the spectral transmission characteristic of the optical filter provided in the filter turret illustrated in FIG. 11.

The optical filter 347 is configured to have a spectral transmission characteristic to transmit V light and B light each having a wavelength Wbb or less at the transmittance TM, as illustrated in FIG. 14, for example. The optical filter 347 is configured to have a spectral transmission characteristic to have a transmittance larger than zero in a wavelength band that is not less than a wavelength Wgb, as illustrated in FIG. 14, for example. The optical filter 347 is configured to have a spectral transmission characteristic to transmit R light having a wavelength Wra or more at the transmittance TM, as illustrated in FIG. 14. The optical filter 347 is configured to have a spectral transmission characteristic to extract from G light to be emitted from the green LED 32c G3 light having an intensity in a wavelength band that is not less than the wavelength Wgb nor more than a wavelength Wge while including wavelengths 540 nm and 580 nm corresponding to a maximum wavelength of an absorbance by hemoglobin and transmit the extracted light at the transmittance TM, as illustrated in FIG. 14. FIG. 14 is a diagram for describing an example of the spectral transmission characteristic of the optical filter provided in the filter turret illustrated in FIG. 11.

In other words, the optical filter 347 is configured to have a spectral transmission characteristic to change a spectrum of the G light to be emitted from the green LED 32c into a spectrum set to reach two layers, that is, an intermediate mucosal layer and a deep mucosal layer at one time in the wavelength band having a high absorbance by hemoglobin.

The optical filter 348 is configured to have the same spectral transmission characteristic as the spectral transmission characteristic of the optical filter 344. More specifically, the optical filter 348 is configured to have a spectral transmission characteristic to transmit lights in all wavelength bands at the transmittance TM, as illustrated in FIG. 6, for example.

In other words, the filter turret 34A is configured as a filter switching mechanism having a function of a spectrum varying section.

Then, functions of the present embodiment will be described below.

First, when a user performs an operation for connecting the sections in the endoscope system 1 to one another to turn on power to the endoscope system 1 and then switching a scope switch 23 and/or an illumination switch provided in an input apparatus 6 from OFF to ON, for example, to instruct a control section 47 to supply illumination light from the light source apparatus 3 to an endoscope 2. The user operates the scope switch 23 and/or the illumination mode change-over switch provided in the input apparatus 6, to instruct the control section 47 to set an illumination mode of the endoscope system 1 to a first illumination mode.

The control section 47 has a function of a light amount adjustment section, and causes each of the LEDs in a light source unit 32 to emit light in a first light emission amount ratio RT1 set to satisfy a setting condition, described below, with a light amount of the G1 light including a spectrum corresponding to a spectral transmission characteristic of the optical filter 345 as a reference while generating an illumination control signal for causing the LEDs to respectively emit lights by time division in a predetermined order and outputting the generated illumination control signal to the light source control section 31 when the control section 47 detects the instruction to set the illumination mode of the endoscope system 1 to the first illumination mode.

The control section 47 generates a filter switching signal for supplying light, which has passed through the optical filter 345, as illumination light and outputs the generated filter switching signal to the light source control section 31 when the control section 47 detects the instruction to set the illumination mode of the endoscope system 1 to the first illumination mode.

Figure 15:
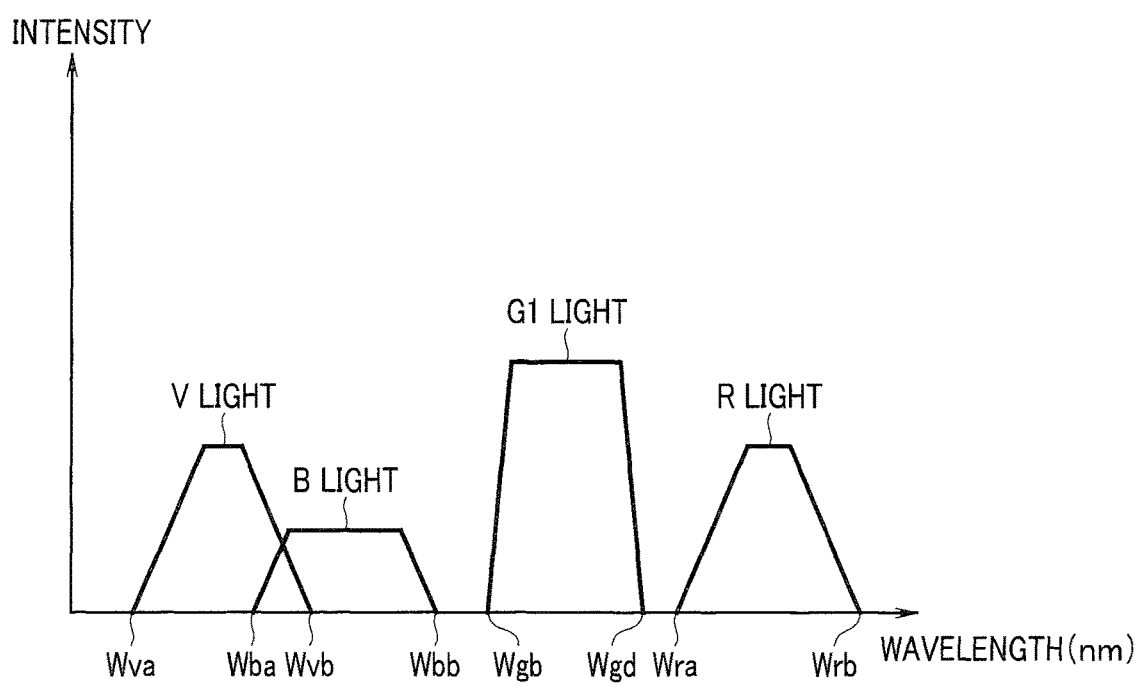
FIG. 15 is a diagram for describing an example of illumination light to be supplied from the light source apparatus in the second embodiment.

The light source control section 31 controls each of the LEDs provided in the light source unit 32 in response to the illumination control signal to be outputted from the control section 47. The light source control section 31 performs control to rotate the filter turret 34A such that the optical filter 345 is inserted into an optical path of light to be emitted via the multiplexer 33 in response to the filter switching signal to be outputted from the control section 47. According to such an operation of the light source control section 31, VB light including V light and B light, G1 light, and R light, as illustrated in FIG. 15, for example, are sequentially supplied as illumination light to the endoscope 2 from the light source apparatus 3 while an image pickup signal obtained by image pickup of return light from an object illuminated with the illumination light is outputted to the processor 4 from an image pickup section 21. FIG. 15 is a diagram for describing an example of illumination light to be supplied from the light source apparatus in the second embodiment.

When a light emission amount of the V light in a first light emission amount ratio RT1 is taken as EV1, a light emission amount of the B light in the first light emission amount ratio RT1 is taken as EB1 (<EV1), and a light emission amount of the R light in the first light emission amount ratio RT1 is set to ER1, light in each of colors to be emitted via the optical filter 345 is adjusted to satisfy a relationship expressed by the following equation (5):

$$\alpha \times (EV1 + EB1) = EG1 = \beta \times ER1 \qquad (5)$$

In other words, the light emission amounts EV1, EB1, and ER1 in the first light emission amount ratio RT1 are set with a light amount EG1 (<EG) of the G1 light to be extracted from the G light having a light emission amount EG as a reference. The control section 47 in the present embodiment respectively adjusts a light amount of the V light to be emitted from the violet LED 32a, a light amount of the B light to be emitted from the blue LED 32b, and a light amount of the R light to be emitted from the red LED 32d based on the first light emission amount ratio RT1 set with the light amount EG1 of the G1 light as a reference in the first illumination mode.

The control section 47 performs similar control to the control in the first embodiment for a color adjustment section 44 and a highlighting processing section 45 when the control section 47 detects the instruction to set the illumination mode of the endoscope system 1 to the first illumination mode. The color adjustment section 44 performs similar color adjustment processing to the color adjustment processing in the first embodiment in the first illumination mode under the control of the control section 47. The highlighting processing section 45 performs similar highlighting processing to the highlighting processing in the first embodiment in the first illumination mode under the control of the control section 47, as described above.

According to the operation as described above, when the illumination mode of the endoscope system 1 is set to the first illumination mode, the respective light amounts of the V light, the B light, and the R light to be supplied to the endoscope 2 from the light source apparatus 3 are adjusted with the light amount EG1 of the G1 light as a reference. According to the operation as described above, when the illumination mode of the endoscope system 1 is set to the first illumination mode, the object is irradiated with illumination light including the G1 light that reaches an intermediate mucosal layer in a deep portion of a mucous membrane of a living tissue and has a high absorbance by hemoglobin while image data IG1 obtained by image pickup of return light from the object illuminated with the G1 light is subjected to color adjustment processing and highlighting processing. Accordingly, according to the operation as described above, when the illumination mode of the endoscope system 1 is set to the first illumination mode, an observation image having a color tone suitable for observation of the intermediate mucosal layer of the living tissue and faithfully reproducing a distribution of hemoglobin in the intermediate mucosal layer can be displayed on the display apparatus 5.

According to the operation as described above, the light emission amount EV1 in the first light emission amount ratio RT1 is set to a light amount larger than the light emission amount EB1 in the first light emission amount ratio RT1. Accordingly, according to the operation as described above, an observation image in which a blood vessel existing in a mucosal surface layer of the living tissue can be more easily observed than the observation image in the first embodiment can be displayed on the display apparatus 5 when the illumination mode of the endoscope system 1 is set to the first illumination mode.

The user operates the scope switch 23 and/or the illumination mode changeover switch provided in the input apparatus 6, to instruct the control section 47 to set the illumination mode of the endoscope system 1 to a second illumination mode.

The control section 47 has a function of a light amount adjustment section, and causes each of the LEDs in the light source unit 32 to emit light in a second light emission amount ratio RT2 set to satisfy a setting condition, described below, with a light amount of G2 light including a spectrum corresponding to a spectral transmission characteristic of the optical filter 346 as a reference while generating an illumination control signal for causing the LEDs to respectively emit lights by time division in a predetermined order and outputting the generated illumination control signal to the light source control section 31 when the control section 47 detects the instruction to set the illumination mode of the endoscope system 1 to the second illumination mode.

The control section 47 generates a filter switching signal for supplying light, which has passed through the optical filter 346, as illumination light and outputs the generated filter switching signal to the light source control section 31 when the control section 47 detects the instruction to set the illumination mode of the endoscope system 1 to the second illumination mode.

Figure 16:
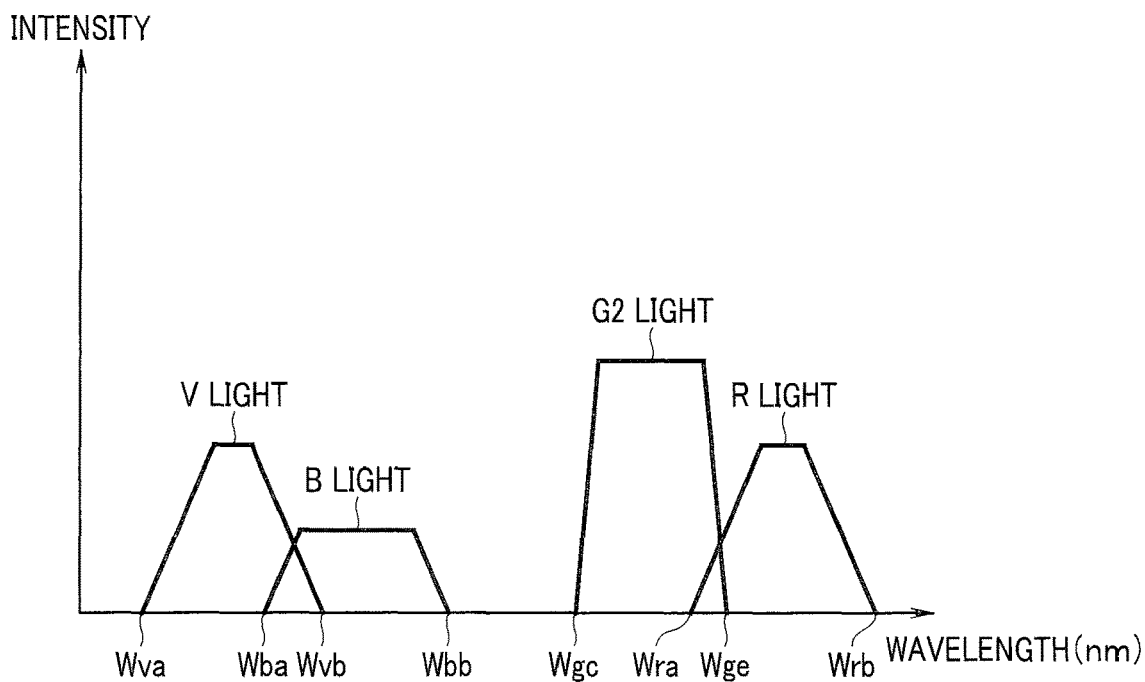
FIG. 16 is a diagram for describing an example of illumination light to be supplied from the light source apparatus in the second embodiment.

The light source control section 31 controls each of the LEDs provided in the light source unit 32 in response to the illumination control signal to be outputted from the control section 47. The light source control section 31 performs control to rotate the filter turret 34A such that the optical filter 346 is inserted into an optical path of light to be emitted via the multiplexer 33 in response to the filter switching signal to be outputted from the control section 47. According to such an operation of the light source control section 31, VB light including V light and B light, G2 light, and R light, as illustrated in FIG. 16, for example, are sequentially supplied as illumination light to the endoscope 2 from the light source apparatus 3 while an image pickup signal obtained by image pickup of return light from the object illuminated with the illumination light is outputted to the processor 4 from the image pickup section 21. FIG. 16 is a diagram for describing an example of illumination light to be supplied from the light source apparatus in the second embodiment.

When a light emission amount of the V light in a second light emission amount ratio RT2 is taken as EV2, a light emission amount of the B light in the second light emission amount ratio RT2 is taken as EB2 (<EV2), and a light emission amount of the R light in the second light emission amount ratio RT2 is taken as ER2, light in each of colors to be emitted via the optical filter 346 is adjusted to satisfy a relationship expressed by the following equation (6):

$$\alpha \mp (EV2 + EB2) = EG2 = \beta \times ER2 \qquad (6)$$

In other words, the light emission amounts EV2, EB2, and ER2 in the second light emission amount ratio RT2 are set with a light amount EG2 (<EG) of the G2 light to be extracted from the G light having the light emission amount EG as a reference. The control section 47 in the present embodiment respectively adjusts a light amount of the V light to be emitted from the violet LED 32a, a light amount of the B light to be emitted from the blue LED 32b, and a light amount of the R light to be emitted from the red LED 32d based on the second light emission amount ratio RT2 set with the light amount EG2 of the G2 light as a reference in the second illumination mode.

The control section 47 performs similar control to the control in the first embodiment for the color adjustment section 44 and the highlighting processing section 45 when the control section 47 detects the instruction to set the illumination mode of the endoscope system 1 to the second illumination mode. The color adjustment section 44 performs similar color adjustment processing to the color adjustment processing in the first embodiment in the second illumination mode under the control of the control section 47. The highlighting processing section 45 performs similar highlighting processing to the highlighting processing in the first embodiment in the second illumination mode under the control of the control section 47, as described above.

According to the operation as described above, when the illumination mode of the endoscope system 1 is set to the second illumination mode, the respective light amounts of the V light, the B light, and the R light to be supplied to the endoscope 2 from the light source apparatus 3 are adjusted with the light amount EG2 of the G2 light as a reference. According to the operation as described above, when the illumination mode of the endoscope system 1 is set to the second illumination mode, the object is irradiated with illumination light including the G2 light that reaches a deep mucosal layer as a layer deeper than the intermediate mucosal layer in the deep portion of the mucous membrane of the living tissue and has a high absorbance by hemoglobin while image data IG2 obtained by image pickup of return light from the object illuminated with the G2 light is subjected to color adjustment processing and highlighting processing. Accordingly, according to the operation as described above, when the illumination mode of the endoscope system 1 is set to the second illumination mode, an observation image having a color tone suitable for observation of the deep mucosal layer of the living tissue and faithfully reproducing a distribution of hemoglobin in the deep mucosal layer can be displayed on the display apparatus 5.

According to the operation as described above, the light emission amount EV2 in the second light emission amount ratio RT2 is set to a light amount larger than the light emission amount EB2 in the second light emission amount ratio RT2. Accordingly, according to the operation as described above, the observation image in which the blood vessel existing in the mucosal surface layer of the living tissue can be more easily observed than the observation image in the first embodiment can be displayed on the display apparatus 5 when the illumination mode of the endoscope system 1 is set to the second illumination mode.

The user operates the scope switch 23 and/or the illumination mode changeover switch provided in the input apparatus 6, to instruct the control section 47 to set the illumination mode of the endoscope system 1 to a third illumination mode.

The control section 47 has a function of a light amount adjustment section, and causes each of the LEDs in the light source unit 32 to emit light in a third light emission amount ratio RT3 set to satisfy a setting condition, described below, with a light amount of G3 light including a spectrum corresponding to a spectral transmission characteristic of the optical filter 347 as a reference while generating an illumination control signal for causing the LEDs to respectively emit lights by time division in a predetermined order and outputting the generated illumination control signal to the light source control section 31 when the control section 47 detects the instruction to set the illumination mode of the endoscope system 1 to the third illumination mode.

The control section 47 generates a filter switching signal for supplying light, which has passed through the optical filter 347, as illumination light and outputs the generated filter switching signal to the light source control section 31 when the control section 47 detects the instruction to set the illumination mode of the endoscope system 1 to the third illumination mode.

Figure 17:
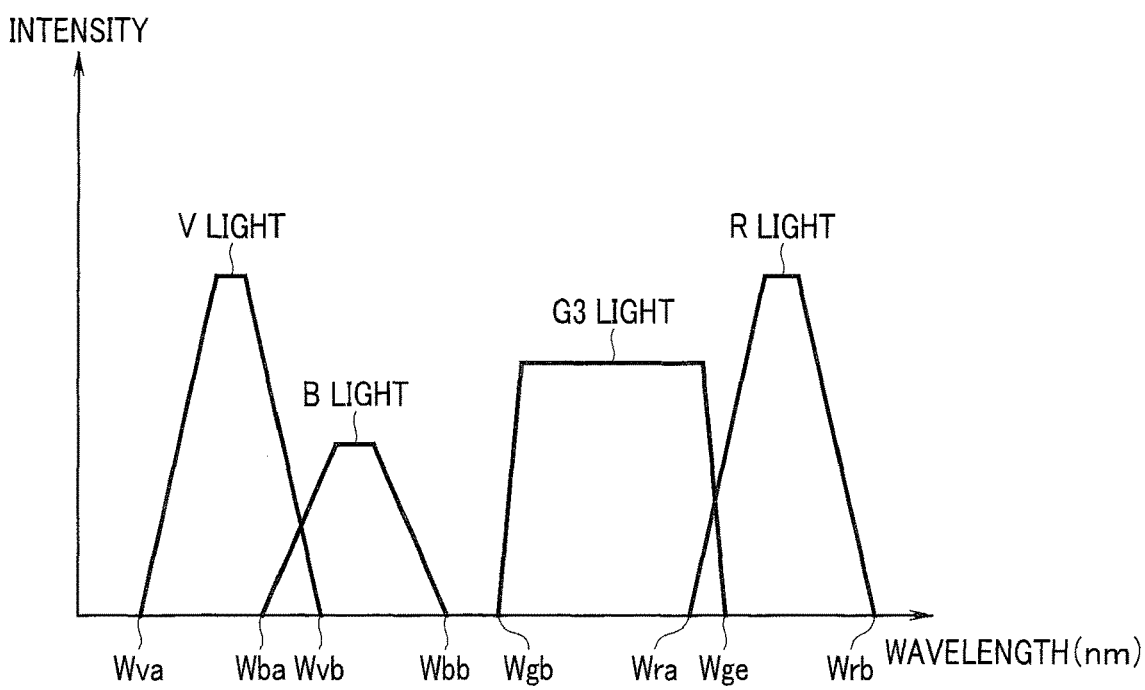
FIG. 17 is a diagram for describing an example of illumination light to be supplied from the light source apparatus in the second embodiment.

The light source control section 31 controls each of the LEDs provided in the light source unit 32 in response to the illumination control signal to be outputted from the control section 47. The light source control section 31 performs control to rotate the filter turret 34A such that the optical filter 347 is inserted into an optical path of light to be emitted via the multiplexer 33 in response to the filter switching signal to be outputted from the control section 47. According to such an operation of the light source control section 31, VB light including V light and B light, G3 light, and R light, as illustrated in FIG. 17, for example, are sequentially supplied as illumination light to the endoscope 2 from the light source apparatus 3 while an image pickup signal obtained by image pickup of return light from the object illuminated with the illumination light is outputted to the processor 4 from the image pickup section 21. FIG. 17 is a diagram for describing an example of illumination light to be supplied from the light source apparatus in the second embodiment.

When a light emission amount of the V light in a third light emission amount ratio RT3 is taken as EV3, a light emission amount of the B light in the third light emission amount ratio RT3 is taken as EB3 (<EV3), and a light emission amount of the R light in the third light emission amount ratio RT3 is taken as ER3, light in each of colors to be emitted via the optical filter 347 is adjusted to satisfy a relationship expressed by the following equation (7):

$$\alpha \times (EV3 + EB3) = EG3 = \beta \times ER3 \qquad (7)$$

In other words, the light emission amounts EV3, EB3, and ER3 in the third light emission amount ratio RT3 are set with a light amount EG3 (<EG) of the G3 light to be extracted from the G light having the light emission amount EG as a reference. The control section 47 in the present embodiment respectively adjusts a light amount of the V light to be emitted from the violet LED 32a, a light amount of the B light to be emitted from the blue LED 32b, and a light amount of the R light to be emitted from the red LED 32d based on the third light emission amount ratio RT3 set with the light amount EG3 of the G3 light as a reference in the third illumination mode.

The control section 47 performs similar control to the control in the first embodiment for the color adjustment section 44 and the highlighting processing section 45 when the control section 47 detects the instruction to set the illumination mode of the endoscope system 1 to the third illumination mode. The color adjustment section 44 performs similar color adjustment processing to the color adjustment processing in the first embodiment in the third illumination mode under the control of the control section 47. The highlighting processing section 45 performs similar highlighting processing to the highlighting processing in the first embodiment in the third illumination mode under the control of the control section 47, as described above.

According to the operation as described above, when the illumination mode of the endoscope system 1 is set to the third illumination mode, the respective light amounts of the V light, the B light, and the R light to be supplied to the endoscope 2 from the light source apparatus 3 are adjusted with the light amount EG3 of the G3 light as a reference. According to the operation as described above, when the illumination mode of the endoscope system 1 is set to the third illumination mode, the object is irradiated with illumination light including the G3 light that reaches two layers, that is, the intermediate mucosal layer and the deep mucosal layer of the living tissue at one time while image data IG3 obtained by image pickup of return light from the object illuminated with the G3 light is subjected to color adjustment processing and highlighting processing. Accordingly, according to the operation as described above, when the illumination mode of the endoscope system 1 is set to the third illumination mode, an observation image having a color tone suitable for observation of a section from the intermediate mucosal layer to the deep mucosal layer of the living tissue can be displayed on the display apparatus 5.

According to the operation as described above, the light emission amount EV3 in the third light emission amount ratio RT3 is set to a light amount larger than the light emission amount EB3 in the third light emission amount ratio RT3. Accordingly, according to the operation as described above, the observation image in which the blood vessel existing in the mucosal surface layer of the living tissue can be more easily observed than the observation image in the first embodiment can be displayed on the display apparatus 5 when the illumination mode of the endoscope system 1 is set to the third illumination mode.

The user operates the scope switch 23 and/or the illumination mode changeover switch provided in the input apparatus 6, to instruct the control section 47 to set the illumination mode of the endoscope system 1 to a fourth illumination mode.

The control section 47 causes each of the LEDs in the light source unit 32 to emit light in a predetermined light emission amount ratio RT while generating an illumination control signal for causing the LEDs to respectively emit lights by time division in a predetermined order and outputting the generated illumination control signal to the light source control section 31 when the control section 47 detects the instruction to set the illumination mode of the endoscope system 1 to the fourth illumination mode.

The control section 47 generates a filter switching signal for supplying light, which has passed through the optical filter 348, as illumination light and outputs the generated filter switching signal to the light source control section 31 when the control section 47 detects the instruction to set the illumination mode of the endoscope system 1 to the fourth illumination mode.

The light source control section 31 controls each of the LEDs provided in the light source unit 32 in response to the illumination control signal to be outputted from the control section 47. The light source control section 31 performs control to rotate the filter turret 34A such that the optical filter 348 is inserted into an optical path of light to be emitted via the multiplexer 33 in response to the filter switching signal to be outputted from the control section 47. According to such an operation of the light source control section 31, VB light including V light and B light, G3 light, and R light, as illustrated in FIG. 7, are sequentially supplied as illumination light to the endoscope 2 from the light source apparatus 3 while an image pickup signal obtained by image pickup of return light from the object illuminated with the illumination light is outputted to the processor 4 from the image pickup section 21.

The control section 47 performs similar control to the control in the first embodiment for the color adjustment section 44 and the highlighting processing section 45 when the control section 47 detects the instruction to set the illumination mode of the endoscope system 1 to the fourth illumination mode. The color adjustment section 44 performs similar color adjustment processing to the color adjustment processing in the first embodiment in the fourth illumination mode under the control of the control section 47. The highlighting processing section 45 performs similar highlighting processing to the highlighting processing in the first embodiment in the fourth illumination mode under the control of the control section 47, as described above.

According to the operation as described above, when the illumination mode of the endoscope system 1 is set to the fourth illumination mode, the object is irradiated with illumination light having a light emission amount ratio to satisfy a relationship expressed by the foregoing equation (1) while an observation image corresponding to return light from the object illuminated with the illumination light can be displayed on the display apparatus 5. Accordingly, according to the operation as described above, when the illumination mode of the endoscope system 1 is set to the fourth illumination mode, an observation image having a similar color tone to the color tone of the observation image in the first embodiment can be displayed on the display apparatus 5.

As described above, according to the present embodiment, an image having a color tone suitable for diagnosis of a lesion existing at a desired depth in the deep portion of the mucous membrane of the living tissue can be acquired.

Note that according to the present embodiment, the LEDs in the light source unit 32 may be caused to concurrently emit lights when a primary color filter that disperses return light incident from an objective optical system 21a into lights in three colors, that is, a red color, a green color, and a blue color is provided on an image pickup surface of an image pickup device 21b, for example.

According to the present embodiment, when the above-described primary color filter is provided on the image pickup surface of the image pickup device 21b, for example, the light source unit 32 may be configured by providing one LED configured to generate broadband light including lights in four colors, that is, V light, B light, G light, and R light instead of the four LEDs that respectively generate the lights in the four colors.

In the present embodiment, respective magnitudes of the light amounts EG1 and EG2 may be made the same by setting the respective transmittances TM of the optical filters 341 and 342 to the same value, for example.

In the present embodiment, the respective magnitudes of the light amounts EG1 and EG2 may be made different from each other by setting the respective transmittances TM of the optical filters 341 and 342 to different values.

The present invention is not limited to the above-described embodiments, and various changes and applications are possible without departing from the scope and spirit of the invention.

What is claimed is:

1. An endoscope system comprising:
a light source configured to generate violet light, blue light, green light, and red light;
a filter switching mechanism configured to be capable of changing a spectrum of the green light emitted from the light source to each of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane, in a wavelength band having a high absorbance by hemoglobin;
a light amount adjustment circuit configured to respectively adjust light amounts of lights in three colors, that is, the violet light, the blue light, and the red light with a light amount of the green light including the spectrum changed by the filter switching mechanism as a reference;
an image sensor configured to pick up an image of return light from an object illuminated with the green light including the spectrum changed by the filter switching mechanism and the lights in the three colors respectively including the light amounts adjusted by the light amount adjustment circuit; and
a highlighting processing circuit configured to subject an image acquired by the image sensor to predetermined highlighting processing corresponding to the spectrum changed by the filter switching mechanism.

2. The endoscope system according to claim 1,
wherein the filter switching mechanism is configured to allow insertion of each of a first optical filter including such a spectral transmission characteristic that the spectrum of the green light is changed to the first spectrum, a second optical filter including such a spectral transmission characteristic that the spectrum of the green light is changed to the second spectrum, and a third optical filter including such a spectral transmission characteristic that the spectrum of the green light is changed to the third spectrum into an optical path of the light emitted from the light source, and the light amount adjustment circuit respectively adjust light emission amounts of the lights in the three colors emitted from the light source based on a first light emission amount ratio set with a light amount of the green light including the first spectrum as a reference, a second light emission amount ratio set with a light amount of the green light including the second spectrum as a reference, and a third light emission amount ratio set with a light amount of the green light including the third spectrum as a reference.

3. The endoscope system according to claim 1,
wherein the first spectrum and the second spectrum overlap each other in a predetermined wavelength band.

4. An endoscope apparatus comprising:
a light source configured to generate violet light, blue light, green light, and red light;
a filter switching mechanism configured to be capable of changing a spectrum of the green light emitted from the light source to each of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin;
a light amount adjustment circuit configured to respectively adjust light amounts of lights in three colors, that is, the violet light, the blue light, and the red light with a light amount of the green light including the spectrum changed by the filter switching mechanism as a reference; and
a highlighting processing circuit configured to subject an image acquired with an image sensor by image pickup of return light from an object illuminated with the green light including the spectrum changed by the filter switching mechanism and the lights in the three colors respectively including the light amounts adjusted by the light amount adjustment circuit to predetermined highlighting processing corresponding to the spectrum changed by the filter switching mechanism.

5. A light source apparatus comprising:
a light source configured to generate violet light, blue light, green light, and red light; and
a filter switching mechanism configured to be capable of changing a spectrum of the green light emitted from the light source to each of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin.

6. A light source apparatus that generates illumination light to an object, the light source apparatus comprising:
a light source configured to generate violet light, blue light, green light, and red light; and
a filter switching mechanism configured to be capable of changing a spectrum of the green light emitted from the light source to each of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin, while respectively adjusting light amounts of lights in three colors, that is, the violet light, the blue light, and the red light with a light amount of the green light including the changed spectrum as a reference.

7. An endoscope system comprising:
a light source configured to generate green light and light in a predetermined color different from the green light;
a filter switching mechanism configured to be capable of changing a spectrum of the green light emitted from the light source to each of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin;
a light amount adjustment circuit configured to adjust a light amount of the light in the predetermined color with a light amount of the green light including the spectrum changed by the filter switching mechanism as a reference;
an image sensor configured to pick up an image of return light from an object illuminated with the green light including the spectrum changed by the filter switching mechanism and the light in the predetermined color including the light amount adjusted by the light amount adjustment circuit; and
a highlighting processing circuit configured to subject an image acquired by the image sensor to predetermined highlighting processing corresponding to the spectrum changed by the filter switching mechanism.

8. An endoscope system comprising:
a first light source as a light source configured to generate green light and configured to be capable of generating the green light including each of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin;
a second light source configured to generate light in a predetermined color different from the green light;
a light amount adjustment circuit configured to adjust a light amount of the light in the predetermined color with a light amount of the green light generated by the first light source as a reference;
an image sensor configured to pick up an image of return light from an object illuminated with the green light generated by the first light source and the light in the predetermined color including the light amount adjusted by the light amount adjustment circuit; and
a highlighting processing circuit configured to subject an image acquired by the image sensor to predetermined highlighting processing corresponding to the spectrum of the green light emitted from the first light source.

9. A method of operating an endoscope system, the method comprising:
generating violet light, blue light, green light, and red light from a light source;
allowing a spectrum of the green light emitted from the light source to be changed to each of a first spectrum including a wavelength band that reaches an intermediate mucosal layer as a first layer within a mucous membrane of a living tissue, a second spectrum including a wavelength band that reaches a deep mucosal layer as a second layer deeper than the first layer within the mucous membrane, and a third spectrum including a wavelength band that reaches two layers, that is, the first layer and the second layer at one time, the first spectrum, the second spectrum, and the third spectrum being set to differ in penetration depth into the mucous membrane in a wavelength band having a high absorbance by hemoglobin;
respectively adjusting light amounts of lights in three colors, that is, the violet light, the blue light, and the red light with a light amount of the green light including the changed spectrum as a reference;
picking up an image of return light from an object illuminated with the green light including the changed spectrum and the lights in the three colors respectively including the adjusted light amounts; and
subjecting an image obtained by image pickup of the return light to predetermined highlighting processing corresponding to the spectrum of the green light emitted from the light source.

* * * * *